United States Patent
Lapidot et al.

(10) Patent No.: US 7,101,708 B1
(45) Date of Patent: Sep. 5, 2006

(54) HEMATOPOIETIC CELL COMPOSITION FOR USE IN TRANSPLANTATION

(75) Inventors: Tsvee Lapidot, Nes-Ziona (IL); Amnon Peled, Tel-Aviv (IL)

(73) Assignee: Yeda Research and Development Co. Ltd., Rehovot (IL)

( * ) Notice: Subject to any disclaimer, the term of this patent is extended or adjusted under 35 U.S.C. 154(b) by 0 days.

(21) Appl. No.: 09/744,654

(22) PCT Filed: Jul. 20, 1999

(86) PCT No.: PCT/IL99/00398

§ 371 (c)(1),
(2), (4) Date: Jan. 29, 2001

(87) PCT Pub. No.: WO00/06704

PCT Pub. Date: Feb. 10, 2000

(30) Foreign Application Priority Data

Jul. 27, 1998 (IL) ...................................... 125532

(51) Int. Cl.
*C12N 5/08* (2006.01)
*C12N 5/02* (2006.01)
*A61K 48/00* (2006.01)

(52) U.S. Cl. ...................... 435/377; 435/373; 435/383; 435/325; 424/93.1; 424/93.2; 530/350

(58) Field of Classification Search ................ 435/325, 435/4, 377, 373, 383; 424/93.1, 93.2; 530/350
See application file for complete search history.

(56) References Cited

U.S. PATENT DOCUMENTS 5,541,103 A * 7/1996 Kanz et al. ............... 435/240.2

FOREIGN PATENT DOCUMENTS

WO          96/15813         5/1996

OTHER PUBLICATIONS

Mohle et al. (1998) Blood, vol. 91, No. 12, 4523-4530.*
Viardot et al. (1997) Blood, vol. 10 Suppl. 1, part 1, 478A.*
Mohle R et al.: "The chemokine receptor CXCR-4 is expressed on CD34+ hematopoietic progenitors and leukemic cells and mediates transendothelial migratioin induced by stromal cell-derived factor-1." BLOOD, vol. 91, No. 12, Jun. 15, 1998, pp. 4523-4530, XP002127667.
Aiuti A et al.: "The chemokine SDF-1 is a chemoattractant for human CD34= hematopoietic progenitor cells provides a new mechanism to explain the mobilization of CD34+ progenitors to peripheral blood." J. Exp. Med., vol. 185, No. 1, Jan. 6, 1997 pp. 111-120, XP000866066.
Larochelle et al.: "Identification of primitive human hematopoietic cells capable of repopulating NOD/SCID mouse bone marrow: Implications for gene therapy." Nature Medicine, vol. 2, No. 12, Dec. 1996 pp. 1329-1337, XP002127668.
Zanjani E et al.: "Human bone morrow CD34-cells engraft in vivo and undergo multilineage expression that includes giving rise to CD34+ cells." Experimental Hematology, vol. 26, No. 4, Aoruk 1998. p. 353, col. 2, line 15-line 20.
Civin C et al.: "Sustained retransplantable, multilneage engraftment of highly purified adult human bone marrow stem cells in vivo." BLOOD, vol. 88, No. 11, Dec. 1, 1996 pp. 4102-4109, XP000866291.
Lapidot T et al.: "Ex-vivo expansion of migrating human CXCR$=SCID repopulating cells by upregulation of surface CXCR4 expression in response to stimulation with SCF or IL-6" BLOOD, vol. 90, No. 10 Supplement 1, 15 Nov. 2, 1998, p. 717a, AP000866556.
Lapidot T et al.: "The chemokine SDF-1 and the cytokine SCF mediate CXCR4 dependant homing of human CD34= CD38-stem cells to the bone marrow of NOD/SCID mice." BLOOD, vol. 92, No. 10 Supplement 1, Nov. 15, 1998, pp. 504a, XP000866555.
Viardot A et al.: "The human immunodeficiency virus (HIV)-type 1 coreceptor CXCDR-4 (fusin) is preferentially expressed on the more immature CD34= hematopoietic stem cells." Annals of Hematology, vol. 77, No. 5, Nov. 5, 1998, pp. 193-197, XP000866301.

* cited by examiner

*Primary Examiner*—Anne Marie S. Wehbe'
(74) *Attorney, Agent, or Firm*—Browdy and Niemark, PLLC

(57) ABSTRACT

Cell compositions consisting essentially of mammalian hematopoietic $CXCR4^+$ stem and progenitor capable to migrate in response to stromal-derived factor 1 (SDF-1) and/or capable to adhere to stromal cells in response to an adhesion-inducing agent, are provided for clinical transplantation. Hematopoietic $CXCR4^{-/low}$ stem and progenitor cells can be converted into $CXCR4^+$ cells by stimulation with a suitable agent. The composition consists preferably of human $CD38^{-/low}$ $CXCR4^+$ cells.

8 Claims, 11 Drawing Sheets

Figure 2A
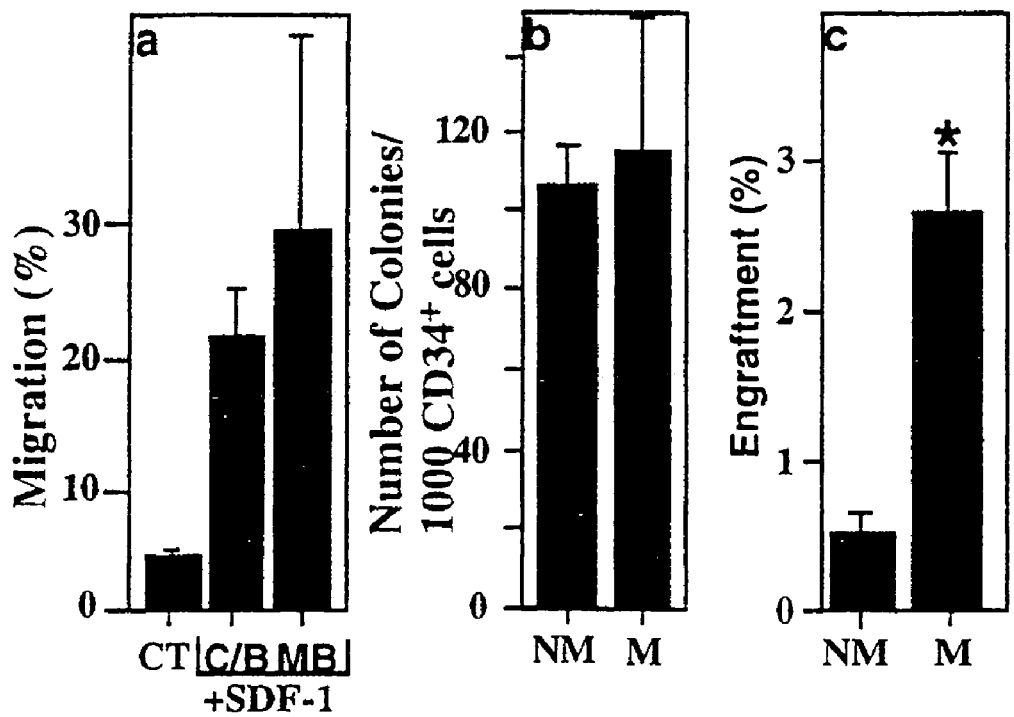
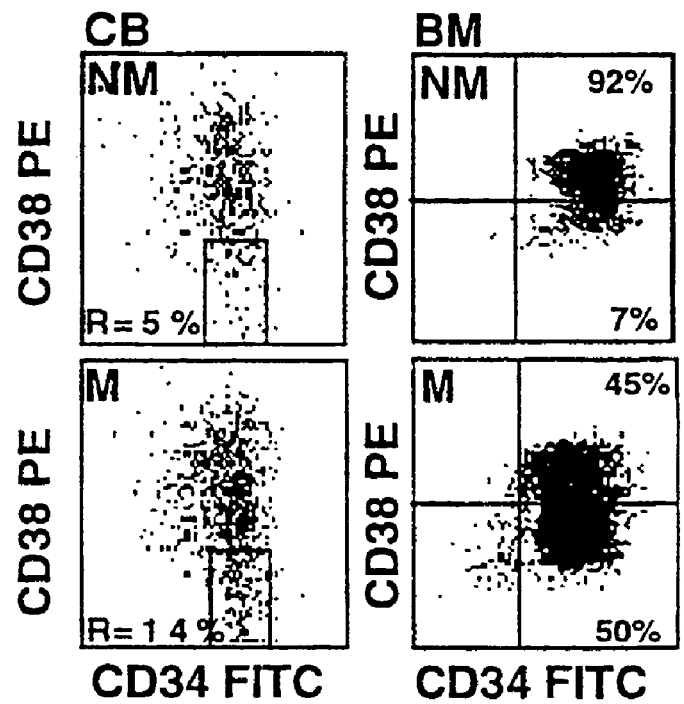

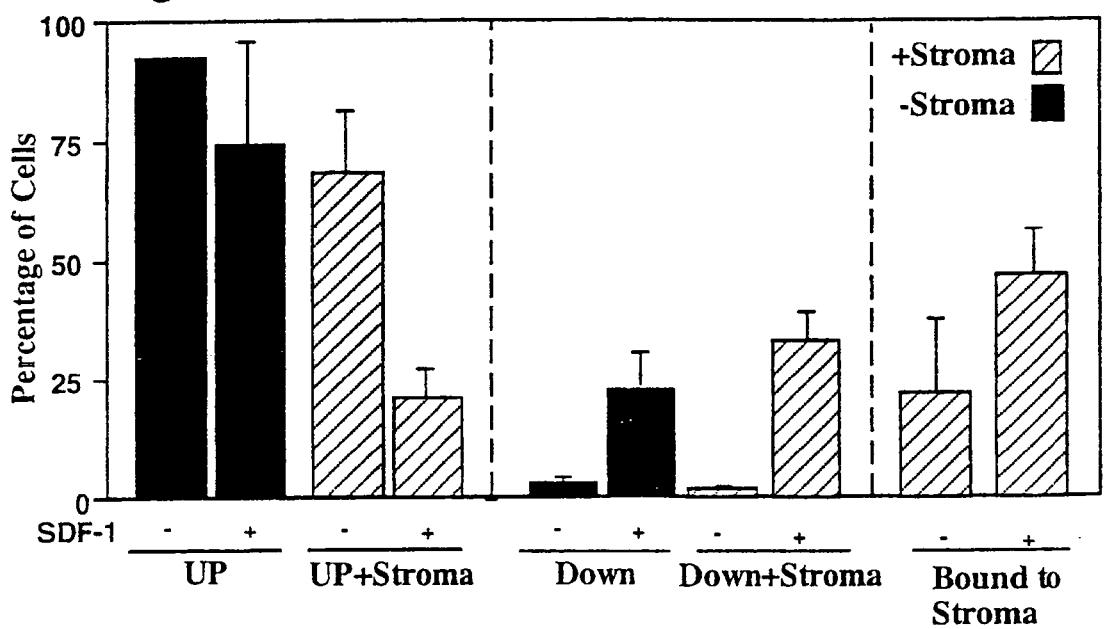
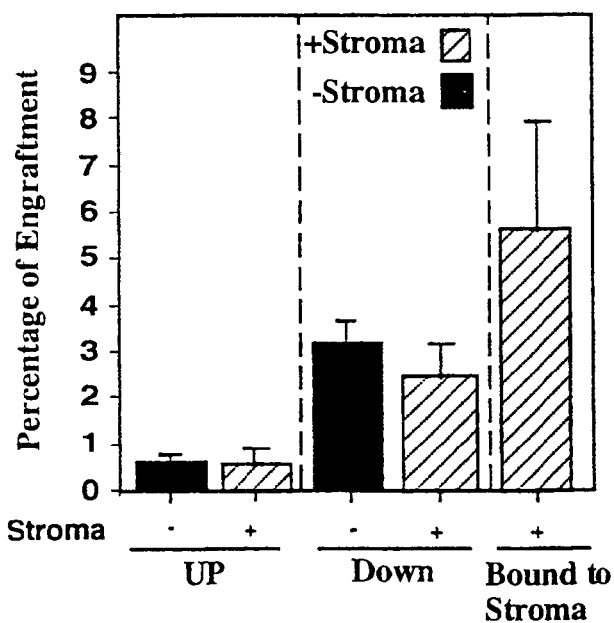

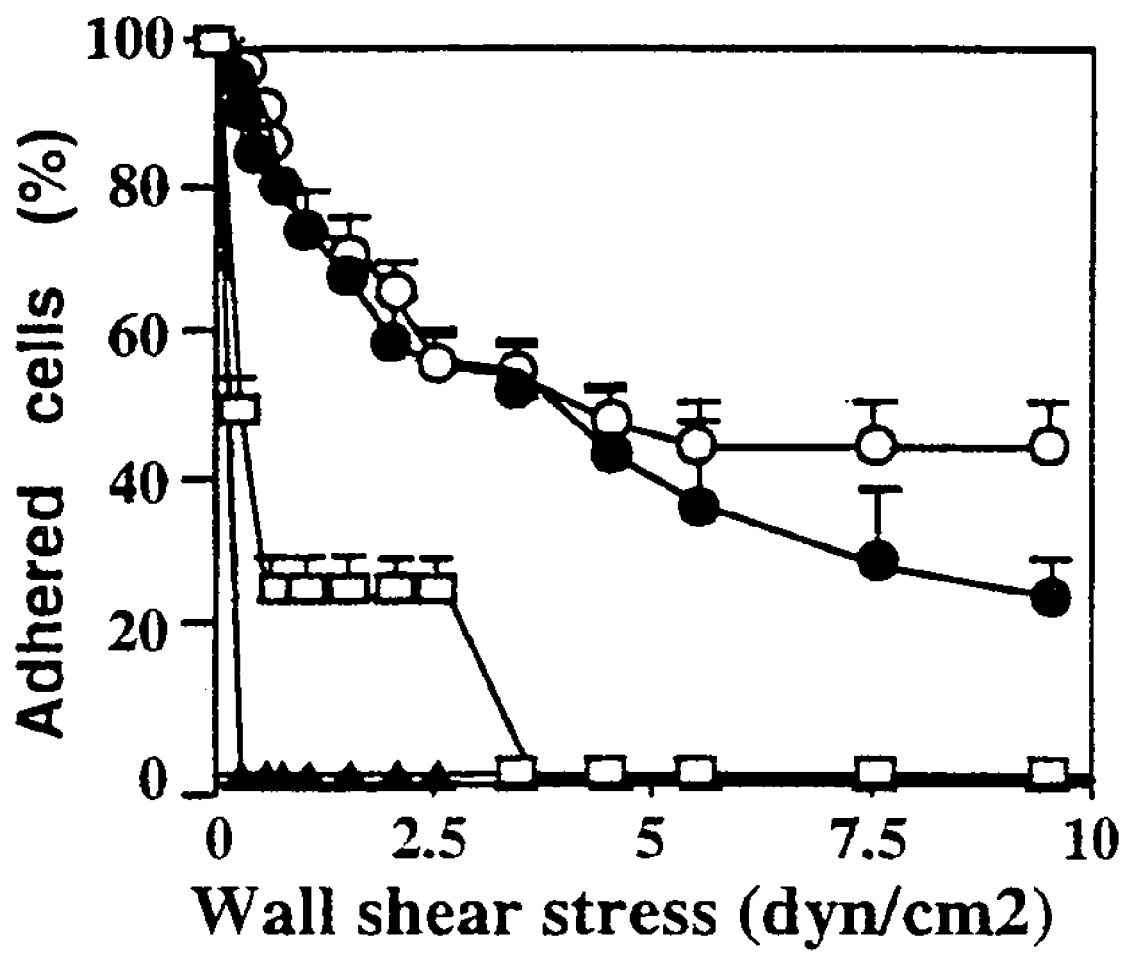

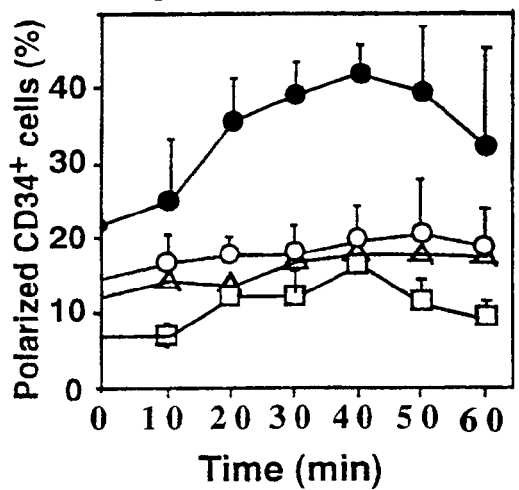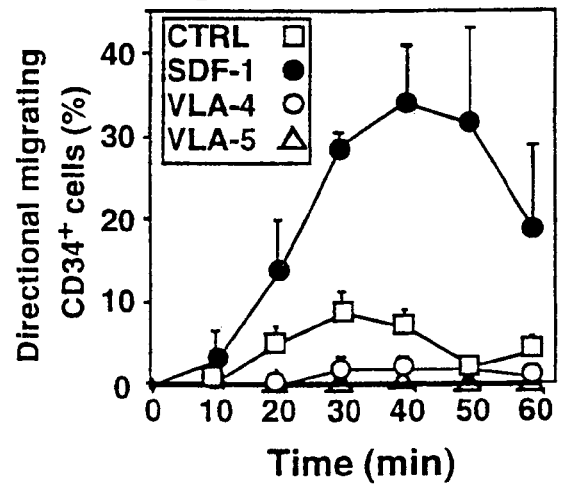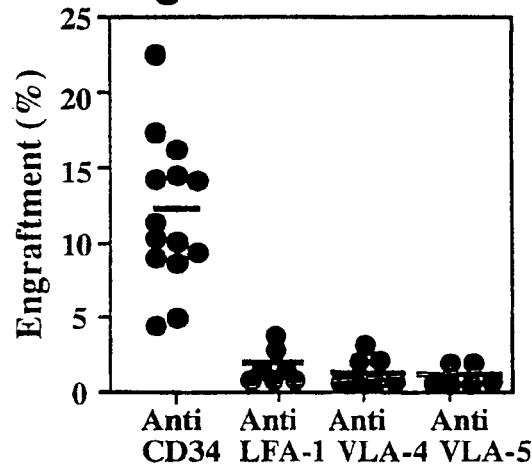

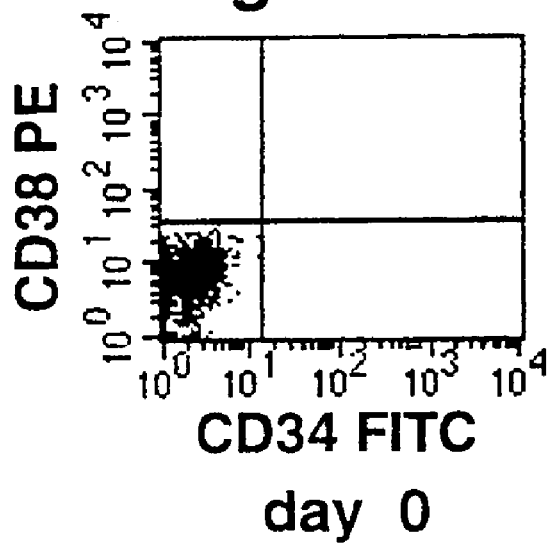
Figure 9A
day 0
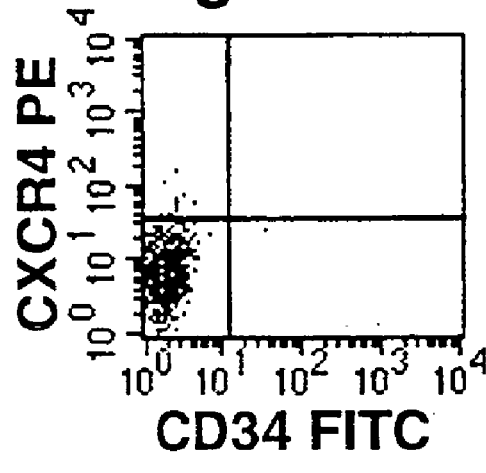
Figure 9B
day 0
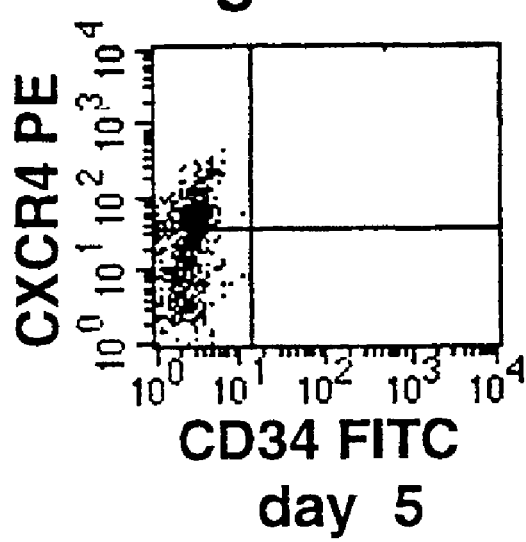
Figure 9C
day 5
Figure 9D
| Day 0 | Day 5 |
|-------|-------|
| 11%   | 45%   |
Migrating primitive CFU-GEMM

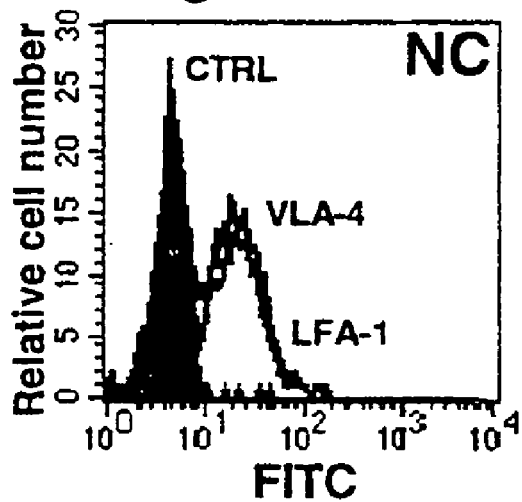
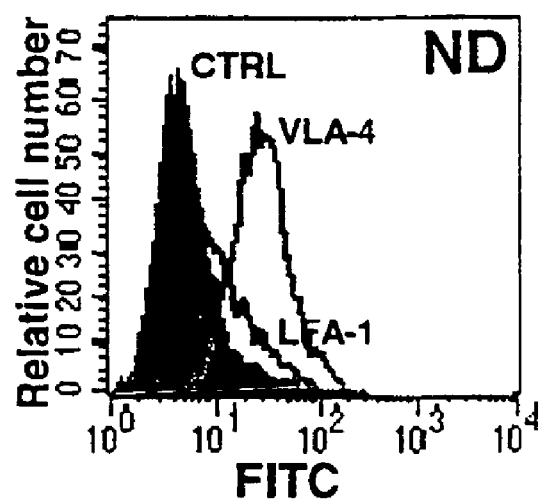
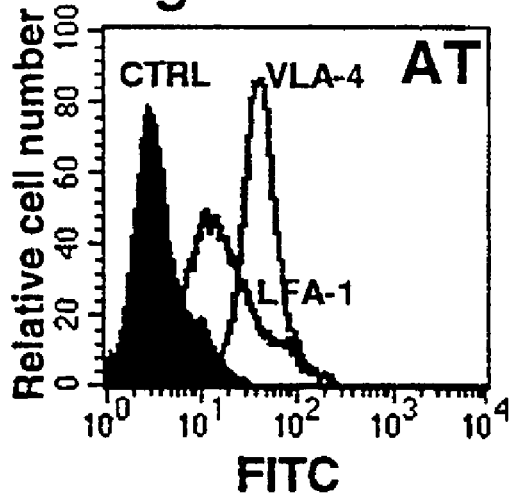
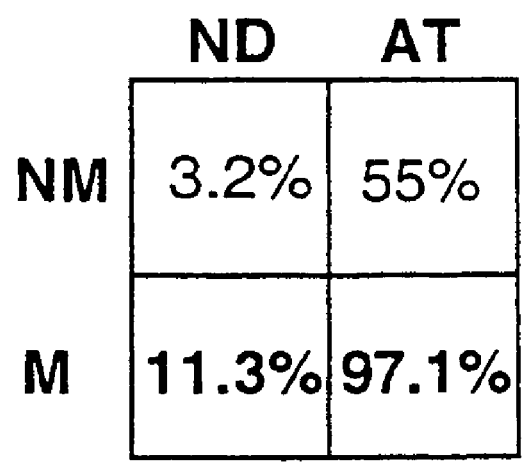

HEMATOPOIETIC CELL COMPOSITION FOR USE IN TRANSPLANTATION

The present application is the national stage under 35 U.S.C. 371 of PCT/IL99/00398, filed 20 Jul. 1999.

FIELD OF THE INVENTION

The present invention relates to compositions comprising hematopoietic cells, more particularly to cell compositions comprising hematopoietic CXCR4$^+$ stem and progenitor cells, and their use in clinical transplantation.

ABBREVIATIONS: BFU-E: burst-forming unit-erythroid; BM: bone marrow; CB: cord blood; CFU-GEMM: colony-forming unit granulocyte/erythrocyte/macrophage/megakariocyte; CFU-GM: colony-forming unit granulocyte-macrophage; CXCR4: SDF-1 receptor; ECM: extracellular matrix; G-CSF: granulocyte-colony stimulating factor; GM-CSF: granulocyte/macrophage-colony stimulating factor; ICAM-1: intracellular cell adhesion molecule-1; IL-6: interleukin-6; LFA-1: lymphocyte function-associated 1; MPB: mobilized peripheral blood; PBL: peripheral blood leukocytes; PMA: phorbol 12-myristate 13-acetate; SCF: stem cell factor; SCID: severe combined immunodeficiency; SDF-1: stromal cell-derived factor 1; SRC: SCID repopulating cell; VLA-4: very late antigen 4; VLA-5: very late antigen 5.

BACKGROUND OF THE INVENTION

Hematopoietic stem cells are rare primitive blood cell progenitors that have the capacity both to self-replicate, so as to maintain a continuous source of regenerative cells, and to differentiate, so as to give rise to various morphologically recognizable precursors of blood cell lineages. These precursors are immature blood cells that cannot self-replicate and must differentiate into mature blood cells including the erythroid, lymphoid and myeloid cells. Within the bone marrow microenvironment, the stem cells self-proliferate and actively maintain continuous production of all mature blood cell lineages throughout life.

Bone marrow (BM) transplantation is being increasingly used in humans as an effective therapy for an increasing number of diseases, including malignancies such as leukemias, lymphoma, myeloma and selected solid tumors as well as nonmalignant conditions such as severe aplastic anemias, immunologic deficiencies and inborn errors of metabolism. The objective of BM transplantation is to provide the host with a healthy stem cell population that will differentiate into mature blood cells that replace deficient or pathologic cell lineages.

The source of the BM for transplantation may be autologous, syngeneic or allogeneic. Preferred are autologous BM or BM from HLA-matched siblings, but also BM from HLA-nonmatched donors is being used for transplantation.

Complicating factors in BM transplantation include graft rejection and graft-vs-host disease (GVHD). Since donor T lymphocytes were found to cause GVHD in animals, one of the procedures to prevent or alleviate GVHD consists in removing T cells from the donor BM before transplantation. This can be done by different techniques, e.g. by soybean agglutination and E-rosetting with sheep red blood cells, or by treatment with anti-T lymphocyte monoclonal antibodies. Extensive use of T-cell depleted BM effectively prevented GVHD but, unfortunately, resulted in a high rate of graft rejection (10–15% in HLA-matched recipients and 50% in HLA-nonmatched recipients) or graft failure (as high as 50%).

Another problem in BM transplantation is the difficulty of achieving long-term successful engraftment also when no graft rejection or GVHD occurs. Nowadays, patients which were successfully transplanted have very low levels of stem cells and immature progenitors which generate mature blood cells, compared with healthy individuals.

Stem cells are functionally defined by their ability to home to the bone marrow and to durably repopulate transplanted recipients with both myeloid and lymphoid cells. The processes that mediate homing and engraftment of human stem cells to the bone marrow involve a complex interplay between cytokines, chemokines and adhesion molecules.

Much of our knowledge of the regulation and the hierarchical organization of the hematopoietic system derives from studies in the mouse wherein stem cells are identified and quantified in long-term reconstitution assays. In contrast, our knowledge of the biology of human hematopoiesis is limited, since it is mostly based on in vitro assays or clinical bone marrow transplantation protocols, both lacking the option to characterize and quantify repopulating stem cells.

Intensive research is being carried out in order to understand the processes that mediate homing and engraftment of human stem cells to the bone marrow. Recently, several groups have established in vivo models for engrafting human stem cells, e.g. into immune deficient mice such as irradiated beige, nude, Xid (X-linked immune deficiency), SCID and non-obese diabetic SCID (NOD/SCID) mice, and in utero transplantation into sheep fetuses, which resulted in successful multilineage engraftment of both myeloid and lymphoid cells (McCune et al., 1988; Nolta et al., 1994; Lapidot et al., 1992; Larochelle et al., 1996; Civin et al., 1996).

Previously, the present inventors have developed a functional in vivo assay for primitive human SCID repopulating cell (SRCs) based on their ability to durably repopulate the bone marrow of intravenously transplanted SCID or NOD/SCID mice with high levels of both myeloid and lymphoid cells (Lapidot et al., 1992; Larochelle et al., 1996). Kinetic experiments demonstrated that only a small fraction of the transplanted cells engrafted and that these cells repopulated the murine bone marrow by extensive proliferation and differentiation. Furthermore, the primitive human cells also retained the capacity to engraft secondary murine recipients (Cashman et al., 1997). Transplantation of populations enriched for CD34 and CD38 cell surface antigen expression, revealed that the phenotype of SRC is CD34$^+$CD38$^-$ (Larochelle et al., 1996). Other repopulating cells may exist since recent studies suggest that immature human CD34$^-$ cells and more differentiated CD34$^+$CD38$^+$ cells have some limited engraftment potential (Zanjani et al., 1998; Conneally et al., 1997).

Accumulating evidence indicates that stem cell homing to the bone marrow is a multistep process. The mechanisms and specific adhesion molecules involved in this process are not fully understood. The β1 integrins very late antigen 4 (VLA-4) and VLA-5 and the β2 integrin lymphocyte function-associated 1 (LFA-1) have been shown to be implicated in the adhesive interactions of both mouse and human progenitor cells with the bone marrow extracellular matrix (ECM), as well as with bone marrow stromal cells (Levesque et al., 1995). VLA-4 plays an especially important role in murine stem cell migration and hematopoiesis in vivo. Murine stem cells lacking β1 integrins fail to colonize the fetal liver (Hirsh et al., 1996).

Similarly, homing of lymphocytes into lymphoid tissue and migration of leukocytes to inflammation sites are also mediated by adhesion molecules and by an entire family of chemoattractant cytokines (chemokines) and their cell surface receptors. Chemokines are cytokines that are best known for their ability to selectively attract subsets of leukocytes to sites of inflammation. However, chemokines are also important regulators of human development, hematopoiesis and angiogenesis. Activation of chemokine receptors in leukocytes results in a multistep process that includes activation of cell surface adhesion molecules followed by firm adhesion to the vessel wall and eventually migration into the extravascular compartment (Premack and Schall, 1996).

Stromal cell-derived factor 1 (SDF-1) is a noted chemokine also known as pre-B cell growth stimulating factor (Nagasawa et al., 1996). Human and murine SDF-1 differ in one amino acid and are crossreactive. SDF-1 is the ligand for the CXCR4 receptor (previously identified as the orphan chemokine receptor fusin/LESTR), which is expressed on many cell types, including some $CD34^+CD38^-$ cells (Bleul et al., 1996). In vitro SDF-1 attracts $CD34^+CXCR4^+$ cells, and was also shown to induce rapid activation of LFA-1 and VLA-4 on human $CD4^+$ T cells (Aiuti et al., 1997; Campbell et al., 1998). In vivo SDF-1 is produced by bone marrow stromal cells as well as by epithelial cells in many organ (Bleul et al., 1996; Aiuti et al., 1997). Mice that lack SDF-1 or do not express CXCR4 exhibit many defects, including the absence of both lymphoid and myeloid hematopoiesis in the fetal bone marrow (Nagasawa et al., 1996). A defect in stem cell homing to the bone marrow may be one explanation for such a phenotype. Overexpression of human CD4 and CXCR4 receptors on murine $CD4^+$ T cells led to enhanced homing of these cells to the murine bone marrow (Sawada et al., 1998).

In view of the expanded approach to treatment of many severe diseases by hematopoietic stem cell treatment, it is highly desirable to understand better the mechanism behind stem cell horning to the bone marrow and repopulation of transplanted hosts in order to obtain stem cells with higher rates of successful and long-tem engraftment.

SUMMARY OF THE INVENTION

It has now been found, according to the present invention, that treatment of human stem cells with antibodies to CXCR4 prevented engraftment of the human stem cells in mice, and that in vitro CXCR4-dependent migration to SDF-1 of $CD38^{-/low}$ cells correlated with in vivo engraftment and stem cell function in mice. These findings indicate that the chemokine SDF-1 and its receptor CXCR4 are critical for murine bone marrow engraftment by immature human repopulating stem cells.

It was further found that SDF-1 in vitro mediates chemotactic migration and integrin activation leading to firm adhesion of the stem and progenitor cells to endothelial ligands and to stromal cells, and that the function of SDF-1 is regulated by the cytokine stem cell factor (SCF). In addition, it was found that SCF induces surface expression of CXCR4 on $CD34^+$ cells and potentiates migration and engraftment and that these processes apparently depend on the major integrins LFA-1, VLA-4 and VLA-5, since antibodies to these integrins interfered with migration and engraftment.

These findings delineate key steps in the complex engraftment process of hematopoietic stem and progenitor cells and suggest up-regulation of CXCR4 expression as a novel approach for improving engraftment of repopulating stem cells in clinical transplantation.

The present invention thus relates, in one aspect, to a cell composition consisting essentially of hematopoietic $CXCR4^+$ stem and progenitor cells capable to migrate in response to SDF-1 and/or capable to adhere to stromal cells in response to an adhesion-inducing agent.

As used herein, the term "$CXCR4^+$ stem and progenitor cells" relates to stem and progenitor cells that express the chemokine receptor CXCR4 on the cell surface at variable levels ranging from low to high. The term "cell composition" in the context of "hematopoietic $CXCR4^+$ stem and progenitor cells" relates to a viable mammalian immature hematopoietic cell composition capable of engraftment and repopulation in a host, consisting essentially of a cellular population of immature hematopoietic $CXCR4^+$ cells being pluripotent stem cells and committed blood progenitor cells. The term "pluripotent stem cells", as used herein, refers to cells that have the capacity to migrate to the bone marrow of a transplanted recipient and to reconstitute the bone marrow and peripheral blood of said recipient with both myeloid and lymphoid lineages and also to proliferate without differentiating (self-renewal), said proliferation being measured by secondary transplantation in which the entire process is repeated in the second recipient. The term "committed progenitor cells", as used herein, refers to blood cell progenitors/precursors that have restricted differentiation and limited self-renewal capacity.

In one embodiment, the cell composition of the invention comprises hematopoietic $CXCR4^+$ stem and progenitor cells capable to migrate in response to SDF-1. In vivo, said migration to SDF-1 occurs through the ECM and is dependent on the β1 integrins VLA-4 and VLA-5. The $CXCR4^+$ stem and progenitor cells further activate the β2 integrin LFA-1, in response to SDF-1.

In another embodiment, the cell composition of the invention comprises hematopoietic $CXCR4^+$ stem and progenitor cells capable to adhere to stromal cells in response to an adhesion-inducing agent. Examples of suitable agents that induce the adhesion of $CXCR4^+$ stem and progenitor cells to stromal cells include chemokines, e.g. SDF-1, macrophage inhibitory protein 1α (MIP-1α) and RANTES; cytokines, e.g. SCF, IL-3, thrombopoietin (TPO) and IL-6; lectins, e.g. PHA and Con A; and phorbol esters, e.g. PMA. In one preferred embodiment, said agent is SDF-1.

The hematopoietic $CXCR4^+$ stem and progenitor cells of the invention may be obtained from hematopoietic $CXCR4^{-/low}$ stem and progenitor cells that have the potential to express CXCR4 on the cell surface upon stimulation with a suitable agent, thus becoming $CXCR4^+$ stem and progenitor cells.

Thus, the invention further comprises a cell composition comprising both hematopoietic $CXCR4^+$ and $CXCR4^{-/low}$ stem and progenitor cells that have the potential to express CXCR4 on the cell surface. Said $CXCR4^{-/low}$ cells are then converted into $CXCR4^+$ cells upon stimulation with a suitable agent before transplantation.

Examples of suitable agents for conversion of the $CXCR4^{-/low}$ into $CXCR4^+$ stem cells are lectins, e.g. phytohemagglutinin (PHA); cytokines/chemokines and stromal cells and mixtures thereof, said cytokines/chemokines and stromal cells being those involved in maintenance, expansion and/or development of stem cells.

Examples of suitable cytokines/chemokines that can be used according to the invention are, without being limited to, SCF, IL-1, IL-6, IL-11 and GM-CSF or a mixture thereof. In preferred embodiments, said cytokine is SCF or a mixture of SCF/IL-6 or of SCF/GM-CSF.

Examples of stromal cells that can be used according to the invention for stimulation of CXCR4$^{-/low}$ cells, are mammalian stromal cells such as, without being limited to, human and murine mesenchymal pre-adipocyte or osteoblast bone-forming stromal cells, or endothelial stromal cells, e.g. the mouse 14F1.1 pre-adipocyte, MBA 2.1 endothelial, and MBA 15.1 osteoblast bone-forming, stromal cell lines. The stromal cells or stromal cell line can be used alone or in a mixture with a cytokine/chemokine such as SDF-1, SCF, IL-1, IL-6, IL-11 or GM-CSF or a mixture of cytokines such as SCF/IL-6 or SCF/GM-CSF. In one preferred embodiment, the stromal cells are used together with SDF-1.

Usually, the CXCR4$^{-/low}$ cells are stimulated with the cytokine or stromal cells or mixtures thereof for a period of days, for example up to 5 days, preferably for 3, most preferably for 1–2 days.

In another aspect, the present invention provides a method for increasing the population of hematopoietic stem and progenitor cells for use in clinical transplantation, which comprises up-regulating surface CXCR4 expression of hematopoietic stem and progenitor cells and sorting out those hematopoietic CXCR4$^+$ stem and progenitor cells that migrate in response to SDF-1. The up-regulation of surface CXCR4 expression may be carried out, for example, by stimulating with a suitable agent a cell composition comprising both hematopoietic CXCR4$^+$ stem and progenitor cells and hematopoietic CXCR4$^{-/low}$ stem and progenitor cells that have the potential to express CXCR4 on the cell surface, thus converting the CXCR4$^{-/low}$ into CXCR4$^+$ cells, and sorting out those hematopoietic CXCR4$^+$ stem and progenitor cells that migrate in response to SDF-1.

In a further aspect, the present invention provides a method for increasing the population of hematopoietic stem and progenitor cells for use in clinical transplantation, which comprises inducung a cellular population of hematopoietic CXCR4$^+$ stem and progenitor cells to adhere to stromal cells in response to an adhesion-inducing agent, e.g. SDF-1, and sorting out those CXCR4$^+$ cells that adhered to the stromal cells in response to said agent.

The hematopoietic CXCR4$^+$ and CXCR4$^{-/low}$ stem and progenitor cells of the compositions of the invention may be autologous, allogeneic human cells from HLA-matched or HLA-nonmatched live donors or cadavers, or xenogeneic cells derived from any suitable non-human mammal such as pig, monkey, etc., but are preferably autologous or allogeneic human cells.

The CXCR4$^+$ and CXCR4$^{-/low}$ stem and progenitor cells may be obtained from a suitable hematopoietic source selected from bone marrow, umbilical cord blood, fetal liver, yolk sac or mobilized peripheral blood cells. Mobilization of bone marrow cells into peripheral blood leukocytes (PBL) may be carried out by leukapheresis after stimulation of the donor with cytokines such as G-CSF or GM-CSF or mixtures of SCF/G-CSF or SCF/GM-CSF.

The hematopoietic CXCR4$^+$ and CXCR4$^{-/low}$ stem and progenitor cells are isolated from their cellular mixtures with mature blood cells in said hematopoietic sources by standard techniques. First, red blood cells are removed, for example, by sedimentation with Ficoll density gradient centrifugation, and mature myeloid cells are removed, for example, with antibodies against mature myeloid antigens (CD33, CD16 and CD13). The thus obtained cells are then treated with antibodies against mature lymphoid antigens to remove the remaining mature cells such as B cells, T cells, and natural killer cells (CD4 and CD8 for T cells, surface Ig for B cells, and CD56 for natural killer cells). Mature cells are removed either by using direct labeled antibodies (e.g. with FITC or PE) against mature antigens and then sorting out by cell sorting, or by negative selection using commercial magnetic bead kits containing antibodies and the mature cells remain in the column with the beads. In this way an enriched population of immature Lin$^-$ cells is obtained that contains the following populations: CD34$^+$CD38$^+$, CD34$^+$CD38$^-$, CD34$^-$CD38$^+$ and CD34$^-$CD38$^-$ that are CXCR4$^+$ and CXCR4$^{-/low}$ cells.

In one embodiment, the thus obtained enriched population of CXCR4$^+$ and CXCR4$^{-/low}$ stem and progenitor cells is then treated with a suitable agent as defined before to convert the CXCR4$^{-/low}$ into CXCR4$^+$ cells, and these cells are submitted to a cell migration assay in a transwell containing a gradient of SDF-1 in the bottom chamber. The CXCR4$^+$ cells with a high migratory capability in response to SDF-1, migrate to the bottom chamber and are sorted out and used for engraftment. By this method, one can obtain enrichment of the composition in stem and progenitor cells capable of engraftment and repopulation from about 25% to >90%, when the source of the hematopoietic cells is bone marrow or cord blood. When the source of the hematopoietic cells are mobilized peripheral blood cells, the in vitro conversion of CXCR4$^{-/low}$ into CXCR4$^+$ cells is highly variable and ranges between converting 5% into greater than 90% or converting 60% into more than 90%. When the agent for conversion of CXCR4$^{-/low}$ into CXCR4$^+$ cells is a cytokine or a mixture of cytokines such as SCF or a mixture of SCF/IL-6 or of SCF/GM-CSF, the cells are incubated with the cytokines before the transwell assay. When the agents are primary human stromal cells or a stromal cell line, the transwell filters are coated with a stromal cell layer, to which part of the CXCR4$^{low}$ and CXCR4$^+$ cells adhere, while other CXCR4$^+$ cells migrate to the bottom chamber within 4 hours, and both are recovered.

In another embodiment for the preparation of the cell composition comprising CXCR4$^+$ stem and progenitor cells, the enriched population of CXCR4$^+$ and CXCR4$^{-/low}$ stem and progenitor cells obtained after removal of the mature cells, is caused to adhere to stromal cells in response to an adhesion-inducing agent, such as SDF-1, for 4 hours, and the cells that adhered to the stromal cells in response to said agent are either sorted out for transplantation or are transplanted together with the stromal cells after trypsinyzation.

In one preferred embodiment of the invention, the cell composition comprises hematopoietic CD38$^{-/low}$CXCR4$^+$ cells, that may be CD34$^+$CD38$^{-/low}$CXCR4$^+$ or CD34$^-$CD38$^{-/low}$CXCR4$^+$ cells. Both CD34$^+$CD38$^{-/low}$ CXCR4$^+$ and CD34-CD38$^{-/low}$CXCR4$^+$ cell subpopulations include cells which have stem cell properties and are suitable for engraftment and constitute preferred embodiments of the invention.

Purification of CD34$^+$ cells may be performed by positive selection using commercial immunomagnetic separation kits and determining purity of the CD34$^+$ cells by FACS analysis. CD34$^-$ or immature Lin$^-$ cells may be enriched by negative selection using commercial immunomagnetic separation kits. Additional enrichment of primitive CD34$^+$CD38$^{-/low}$ cells or Lin$^-$CD38$^{-/low}$ cells may be performed by cell sorting using direct labeled antibodies or by commercial immunomagnetic separation systems.

The CD38$^{-/low}$CXCR4$^+$ cells may be obtained from the immature Lin$^-$ cells, obtained after removal of the mature cells, by treatment with antibodies to CD38. By treatment of the Lin⁻ cells with antibodies both to CD34 and CD38, followed by sorting out of the desired CD34⁺ or CD34⁻ cells, CD34⁺ CD38$^{-/low}$ CXCR4⁺ or CD34⁻ CD38$^{-/low}$ CXCR4⁺ cells, respectively, are obtained. In convenient preferred embodiments, CD34⁺ CXCR4⁺, CD34⁻ CXCR4⁺ and Lin⁻ (CD34⁺+CD34⁻)CXCR4⁺ cells containing both CD38$^{-/low}$ and CD38$^{high}$ subpopulations, are used. CD34⁺ cells, for example, consist of 75–99% of CD34⁺CD38$^{high}$ subpopulation and 1–25% of CD34⁺CD38$^{-/low}$ subpopulation, depending on the original source of the hematopoietic cells.

In another aspect, the invention provides a chimeric non-human mammal transplanted with a cell composition of the invention comprising human hematopoietic CXCR4⁺ stem and progenitor cells, said chimeric non-human mammal being capable of supporting the proliferation and differentiation of the transplanted human stem and progenitor cells into all mature blood cells, including myeloid and/or lymphoid cells. This chimeric non-human mammal serves as a model for testing the engraftment efficiency of human hematopoietic CXCR4⁺ stem and progenitor cells according to the invention, by testing the levels of immature human stem cells and blood progenitor cells (for example, BFU-E, CFU-GM and CFU-GEMM) as well as mature human myeloid and lymphoid cells in the mammal, after transplantation of the human CXCR4⁺ cells tested.

In one embodiment, the chimeric non-human mammal is a mouse transplanted with a cell composition consisting of human hematopoietic CD38$^{-/low}$ CXCR4⁺ stem and progenitor cells, that may be CD34⁺ CD38$^{-/low}$ CXCR4⁺ and/or CD34⁻ CD38$^{-/low}$ CXCR4⁺ cells. According to the invention, it is also envisaged to use these cell populations comprising also CD38$^{high}$ CXCR4⁻ cells.

The engraftment of the human cells in the chimeric non-human mammal is carried out by a process comprising:
(a) sublethally irradiating an immunodefficient non-human mammal lacking a population of functional B and T cells; and
(b) transplanting into the irradiated immunodefficient non-human mammal the desired human hematopoietic CXCR4⁺ stem and progenitor cells.

The chimeric non-human mammal may be a mouse, for example, a NOD/SCID or a NOD/SCID β2-microglobulin-knock out (NOD/SCID β2M KO) mouse.

In still another aspect, the invention relates to an in vitro method for screening human immature hematopoietic cells derived from bone marrow, cord blood, fetal liver, yolk sac or mobilized peripheral blood cells, as candidates for transplantation into human hosts, said method comprising:
(a) measuring the level of cell surface CXCR4 expression in a separate sampling of cells with labeled anti-CXCR4 monoclonal antibodies;
(b) increasing, if necessary, the level of CXCR4⁺ cells in the original sample by stimulation of CXCR4$^{-/low}$ cells with a suitable agent;
(c) measuring the CXCR4⁺ cells' ability to migrate in response to SDF-1 and/or to adhere to stromal cells in response to an adhesion-inducing agent, and
(d) sorting out the CXCR4⁺ cells with a high migratory capability in response to SDF-1 and/or the cells which adhered to the stromal cells, these being the cells suitable for successful transplantation into human hosts.

In yet still another aspect, the invention relates to an in vivo method for testing and ascertaining the engraftment capability of human hematopoietic CXCR4⁺ stem and progenitor cells derived from bone marrow, cord blood, fetal liver, yolk sac or mobilized peripheral blood cells, said CXCR4⁺ cells having a high migratory capability in response to SDF-1 or adhering to stromal cells in response to an adhesion-inducing agent, said method comprising:
(a) sublethally irradiating an immunodefficient non-human mammal lacking a population of functional B and T cells;
(b) transplanting said human hematopoietic CXCR4⁺ stem and progenitor cells into the irradiated immunodefficient mammal of (a); and
(c) measuring the level of mature human blood cells including myeloid and/or lymphoid cells in the obtained chimeric non-human mammal;

whereby stable engraftment in the model chimeric non-human mammal capable of supporting the proliferation and differentiation of said transplanted cells into all mature human blood cells, including myeloid and/or lymphoid cells, indicates the suitability of said cells for successful engraftment into human hosts.

A further aspect of the present invention relates to a method for transplantation of immature hematopoietic cells in a patient in need therefor, said method comprising:
(i) conditioning the patient under sublethal, lethal or supralethal conditions; and
(ii) transplanting the conditioned patient with a cell composition consisting essentially of human hematopoietic CXCR4⁺ stem and progenitor cells capable to migrate in response to SDF-1 and/or capable to adhere to stromal cells in response to an adhesion-inducing agent.

The cells may be autologous or allogeneic cells a HLA-matched or HLA-nonmatched live donor or cadaver. The HLA-nonmatched donor may be an unrelated person to the family, but preferably is a very close relative such as one of the parents, a brother or a sister of the patient. Preferably, the human CXCR4⁺ stem cells are obtained from bone marrow or from mobilization of bone marrow cells into peripheral blood leukocytes by leukapheresis after stimulation of the donor with a suitable cytokine such as G-CSF or GM-CSF or each of them in combination with SCF. In one embodiment, the human CXCR4⁺ stem cells are T cell-depleted by techniques well-known in the art. The transplanted cells are preferably CD38$^{-/low}$CXCR4⁺cells, that may be CD34⁺ CD38$^{-/low}$CXCR4⁺ cells and/or CD34⁻CD38$^{-/low}$CXCR4⁺, and may also include CD38$^{high}$ cells.

The host patient is conditioned under sublethal, lethal or supralethal conditions, for example by total body irradiation (TBI) and/or by treatment with myeloablative and immunosuppressive agents according to standard protocols. For example, a sublethal dose of irradiation is within the range of 3–7 Gy TBI, a lethal dose is within the range of 7–9.5 Gy TBI, and a supralethal dose is within the range of 9–16.5 Gy TBI. Examples of myeloablative agents are busulphan, dimethyl mileran and thiotepa, and of immunosuppressive agents are prednisone, methyl prednisolone, azathioprine, cyclosporine, cyclophosphamide, etc.

The method of the invention is suitable for the treatment of diseases curable by bone marrow transplantation such as malignant diseases, including leukemias such as acute lymphoblastic leukemia (ALL), acute nonlymphoblastic leukemia (ANLL), acute myelocytic leukemia (AML) and chronic myelocytic leukemia (CML); severe combined immunodeficiency syndromes (SCID) including adenosine deaminase (ADA) deficiency; osteopetrosis, aplastic anemia, Gaucher's disease, thalassemia and other congenital or genetically-determined hematopoietic abnormalities.

A further application of the invention is in the treatment of malignant diseases such as breast cancer and CML by purging malignant cells from the patient's blood and transplanting into the patient his own hematopoietic cells purged from the malignant ones. The method is applicable for the types of cancers which malignant cells do not migrate to a chemotactic gradient of SDF-1.

Thus, according to this aspect of the invention, there is provided a method for the preparation of a composition of hematopoietic CXCR4$^+$ stem and progenitor cells capable to migrate in response to SDF-1 for autologous transplantation to a cancer patient, by ex vivo purging of malignant cells from said cancer patient while maintaining and enriching for normal hematopoietic CXCR4$^+$ stem cells and progenitors, said method comprising:

(i) providing hematopoietic stem and progenitor cells from a cancer patient, the malignant cells of which patient do not migrate to a chemotactic gradient of SDF-1;

(ii) stimulating said hematopoietic stem and progenitor cells with a suitable agent to enhance the CXCR4 surface expression and response to SDF-1 of said cells;

(iii) carrying out an in vitro transmigration assay with the stimulated hematopoietic CXCR4$^+$ stem and progenitor cells of (ii) to a gradient of SDF-1 across a mechanical barrier of cells such as stromal cells or a stromal cell line, in order to prevent spontaneous non-specific migration of malignant cells;

(iv) washing the migrating cells to remove SDF-1; and (v) isolating the cells obtained in (iv), said cells being CXCR4$^+$ hematopoietic stem and progenitor cells responsive to migration to SDF-1 and purged from the patient's malignant cells, and suitable for autologous transplantation.

In the case of CML patients, the hematopoietic cells of the patient are taken from CML patients after intensive chemotherapy.

The cell composition of the invention may also be used for correction of genetic defects. In this aspect, the invention provides a method for the preparation of a cell composition consisting essentially of hematopoietic CXCR4$^+$ stem and progenitor cells capable to migrate in response to SDF-1, for autologous transplantation for the correction of genetic abnormalities, said method comprising:

(i) introducing a normal gene in hematopoietic CXCR4$^+$ stem and progenitor cells that migrate in response to SDF-1, from a patient having a genetic disorder;

(ii) stimulating said transformed cells of (i) with a suitable agent to enhance their CXCR4 surface expression and response to SDF-1;

(iii) carrying out an in vitro transmigration assay with the stimulated transformed cells of (ii) to a gradient of SDF-1 across a mechanical barrier of cells such as stromal cells or a stromal cell line;

(iv) washing the migrating transformed cells to remove SDF-1; and (v) isolating the transformed cells obtained in (iv), said cells being hematopoietic CXCR4$^+$ stem and progenitor cells responsive to SDF-1 containing the normal gene and being suitable for autologous transplantation to correct the patient's genetic disorder.

In both methods described above, the cells will be derived preferably from the patient's own bone marrow or mobilized peripheral blood cells, and the patient will be conditioned for the transplantation as described before.

DESCRIPTION OF THE FIGURES

FIG. 1A (panel a): Human cord blood CD34$^+$ cells treated for 30 minutes with anti-CXCR4 or with anti-CD34 (control) were transplanted into NOD/SCID mice. Alternatively, anti-SDF-1 was coinjected (i.v.) with the cells and reinjected (i.p.) 24 hours later. After 2 weeks, human progenitor cells were quantified in semi-solid media assays. The following cell types were counted: CFU-GM (white bars), BFU-E (dashed bars), and CFU-GEMM (striped bars). Data are average ±SE (*P<0.01, as determined by paired Student's t test) of 3 experiments. (panel b): Human BM (black bars) or MPB (stippled bars) CD34$^+$ cells were treated with anti-CD34 and anti-CXCR4 antibodies and transplanted into NOD/SCID mice, and total human progenitors were quantified after one month as for Panel a.

FIG. 1B: Anti-CXCR4 antibodies were injected at the indicated times (30 min, 1 day and 4 days) after transplantation of NOD/SCID mice with CB CD34$^+$ cells. Control cells were incubated with anti-CD34. After 2 weeks, bone marrow was assayed for human DNA by Southern blot with the human-specific α satellite probe p17H8. Each lane represents DNA extracted from the bone marrow of one transplanted mouse.

FIG. 1C: CB CD34$^+$ cells were either not treated (CT) or treated for 24 hours with SDF-1 or PMA. (panel a): CXCR4 surface expression of CD34$^+$ cells. (panel b): Transwell migration assay of untreated cells without SDF-1 (CT–) or with SDF-1 (CT+), and migration to SDF-1 of treated cells. (panel c): The percent of human cells in NOD/SCID mice 1 month after transplantation was determined by FACS analysis with antibodies to human CD45. Data are average ±SE (*P<0.01, as determined by paired Student's t test) of 3 experiments.

FIGS. 2A–2B show that SDF-1 induces the migration of SRCs. FIG. 2A (panel a): Transwell migration assay with CD34$^+$ cord blood (C), bone marrow (B), or mobilized peripheral blood (MB) cells. CT, migration without SDF-1. SDF-1 migrating (M) and nonmigrating (NM) cells were assayed for progenitors (panel b) or transplanted into. NOD/SCID or $\beta_2$-microglobulin knockout NOD/SCID mice (panel c). The percent of human cells was quantified as in FIG. 1C, panel c. Data are average ±SD of 11 (panel a) or 3 experiments (panel b), or average ±SE of 3 experiments (Panel c) (*P<0.01). (Panels CB and BM): SDF-1 preferentially induces migration of CD34$^+$CD38$^{-/low}$CXCR4$^+$ cells. Surface expression of CD38 on cord blood (panel CB) and bone marrow (panel BM) CD34$^+$ cells, stained with CD34 FITC and CD38 PE antibodies, was analyzed by flow cytometry on SDF-1 migrating (M) or nonmigrating (NM) cells. R gates CD34$^+$CD38$^-$ cells. FIG. 2B. Sorted cord blood CD34$^+$/CD38$^{-/low}$ cells. (panel a) SDF-1 migrating (M) or nonmigrating (NM) cells were transplanted into NOD/SCID mice. After 6 weeks, percent of engraftment was quantified as in FIG. 1C, panel c. Data are average ±SE (*P<0.01) of 3 experiments. Phenotype analysis of engrafted M and NM cells. Numbers indicate percent of human cells. (panels Ma and Mb) The presence of human lymphoid CD45$^+$CD19$^+$ pre-B cells, stained with CD45 FITC and CD19 PE antibodies, (panel Ma) and progenitors for human CD45$^+$CD56$^+$ natural killer cells, stained with CD45 FITC and CD56 PE antibodies, (panel Mb) is shown.

FIG. 3A: MPB CD34+ cells stained control antibody (curve a) or with CXCR4 PE antibody before (curve b) or after (curve c) 40 hours of treatment with SCF. FIG. 3B: SDF-1 transwell migration of untreated (0), SCF-treated (16 and 40 hours), or control cells cultured for 40 hours without SCF (CT). Data are average ±SE of 3 experiments. FIG. 3C: Percent of engraftment in NOD/SCID mice transplanted with ($2 \times 10^5$) cells before (0) or after 16 or 40 hours of exposure to SCF and 40 hours of exposure to SCF followed by incubation with anti-CXCR4 (+ anti CXCR4). Control cells (CT) as in FIG. 3B. Percent of engraftment was quantified as in FIG. 1C, panel c. Data are average ±SE (*P<0.01, SCF 40 hours versus 0 hours, SCF+ anti-CXCR4, and CT 40 hours) of 3 mice per treatment, in a representative experiment. FIG. 3D: Exposure times of human MPB CD34+ cells to SCF as in FIG. 1C. At time 0 and after 16 hours $1 \times 10^5$ cells per mouse were transplanted, and after 40 hours $0.5 \times 10^5$ cells per mouse were transplanted. Human engraftment was quantified after 1 month by Southern blot analysis.

FIG. 4A: Sorted CB CD34+CD38$^{-/low}$ cells migrating toward SDF-1 were transplanted into NOD/SCID mice (M). Non-migrating cells were either injected directly (NM) or treated with SCF for 48 hours and then injected (+SCF). After 6 weeks, engraftment levels were quantified as in FIG. 1C, panel c. Data in the left panel are average ±SE (*P<0.01) of 4 experiments. FACS analysis of engrafted CD34+CD38$^{-/low}$ cells from mice transplanted with NM cells or transplanted with SCF-treated NM cells (+SCF) are shown. FIG. 4B: BM cells from mice transplanted 4 to 6 weeks before with human CB CD34+ cells in panels a and b were retransplanted untreated ($2^{nd}$ in panel a) or after SCF/IL-6 treatment for 48 hours (panel b) into secondary $\beta_2$-microglobulin knockout NOD/SCID mice. Data in panels a and b are the average ±SE of 4 experiments (panel a, P<0.01, $1^{st}$ versus $2^{nd}$; **P<0.05, $2^{nd}$ in panel b versus $2^{nd}$ in panel a). (panel c) Human CXCR4 expression on CB cells, stained with CXCR4 PE antibody, from transplanted mice immediately labeled (solid) or after 48 hours treatment with SCF/IL-6 (open). (panel d) SDF-1 migration of CB cells from the marrow of transplanted mice before and after treatment with SCF and IL-6 for 48 hours. Data in panel d are the average of triplicates in a representative experiment. FIG. 4C: CB CD34+ cells were stained with control antibody (curve a) or antibody to CXCR4 after a 48-hour exposure to SCF (curve b) or SCF and IL-6 (curve c). Percent of engraftment in (A) and (B) was quantified as in FIG. 1C, panel c.

FIGS. 5A–5B show that SDF-1 stimulates the adhesion and trans-stromal migration of CD34+ progenitors and increases the number of SRCs. FIG. 5A: Migration and adhesion to stroma of human CB CD34+ cells in an assay performed in transwells with bare filters (–Stroma, black bars) or with filters coated with stromal cells (+Stroma, striped bars), without (–) or with (+) a gradient of SDF-1. UP (left): nonmigrating cells that remained in the upper chamber; Down (middle): cells that migrated to the lower chamber when the migration assay was performed in the presence and absence of stroma. Bound to stroma (right): cells that adhered to the stromal cells FIG. 5B: Percent of engraftment in NOD/SCID mice of the nonmigrating, migrating and adhered cells of FIG. 5A.

FIG. 6 shows that SDF-1 induces shear-resistant adhesion of CD34+CXCR4+ cells to ICAM-1. Purified CB CD34+ cells briefly treated with SDF-1 (black diamonds), SDF-1+ EDTA (triangles), PMA (circles), or left untreated (squares), were perfused into a parallel plate flow chamber and allowed to settle for 1 minute at 37° C. on substrates coated with ICAM-1-Fc fusion protein immobilized on protein A. Following attachment, flow was initiated at 1 dyn/cm$^2$ and then the flow was increased step-wise in 2- to 2.5-fold increments every 5 seconds. The number of cells bound at the end of each shear flow interval of incremented shear stress was expressed as percentage relative to the number of attached cells prior to flow initiation. The data represent the average of three experiments ±SE.

FIGS. 7A–7C show the contribution of $\beta 1$ and $\beta 2$ integrins to in vitro migration of CD34+ cells through the ECM and engraftment in vivo. FIG. 7A: Percent polarization of purified cord blood CD34+ cells applied to migration chambers containing ECM-like 3-D gels. FIG. 7B: Percentage of cells migrating toward a gradient of SDF-1. Untreated cells (triangles); cells treated with a gradient of SDF-1 (black diamonds) and CD34+ cells pre-stained with anti-VLA-4 mAb (5 µg/ml) (circles) or anti-VLA-5 mAb (5 µg/ml) (squares) and treated with a gradient of SDF-1 are shown in FIGS. 7A–7B. Purified cord blood CD34+ cells were pre-treated with anti-LFA-1, anti-VLA-4, and anti-VLA-5 mAbs (5 µg/ml) for 30 minutes and transplanted into NOD/SCID mice. Levels of engraftment were estimated by immunostaining with anti-human CD45 mAb (FIG. 7C). The results shown in FIGS. 7A–7B represent the mean average of 3 different experiments ±SD. In FIG. 7C, each point represents data obtained from one mouse and results were pooled from three different experiments.

FIG. 8A: Percentage of human cord blood CD34+ cells ($2 \times 10^5$) engrafted immediately or 48 hours after irradiation of NOD/SCID mice at 375 R, as assayed after 30 days by staining the mouse bone marrow with antibodies to human CD45. FIG. 8B: Percentage of human cord blood CD34+ cells that migrated in response to the bone marrow fluid collected immediately 0 or 4, 24, or 48 hours after irradiation of NOD/SCID mice at 375 R, in a transwell migration assay with the BM fluid in the bottom chamber. FIG. 8C: PCR analysis of the expression, by murine bone marrow stromal cells, of SDF-1 and of actin (control), at different time points following irradiation of the mice.

FIGS. 9A–9D show that CD34−CD38$^{-/low}$ cells pretreated with SCF and IL-6 for 5 days upregulate CXCR4 expression and increase migration to SDF-1 of primitive CFU-GEMM progenitors. FIG. 9A: FACS analysis of purified CD34− CD38− cells from human cord blood. FIG. 9B: FACS analysis of CD34−CD38− cells stained with antibodies to CXCR4 right after purification (day 0). FIG. 9C: FACS analysis of CD34−CD38− cells treated for 5 days with a mixture of SCF/IL-6 and stained with antibodies to CXCR4 at day 5. FIG. 9D: Migration at day 0 vs day 5 of CD34− CD38− cells treated with SCF and IL-6 to a gradient of SDF-1 in transwells. Migrating cells were plated in semi-solid and the numbers of primitive CFU-GEMM mixed colonies were counted. Treatment with SCF- and IL-6 increased the levels of CXCR4 and of migrating CD34− CD38− cells. Engraftment of CD34− cells was dependent on CXCR4 expression (data not shown).

FIGS. 10A–10D show purging of leukemic (CML) stem cells by integrin-dependent migration and/or adhesion to SDF-1. FIG. 10A: Normal CD34+-enriched cells (normal cells: NC) were stained with an unspecific FITC-labeled isotype control antibody (CTRL) as a negative control, with an anti-VLA-4 antibody as a positive control (VLA-4) and with an anti-LFA-1 antibody, before FACS analysis. FIG.

10B: CD34$^+$ enriched cells from a newly diagnosed (ND) CML patient were stained with the same antibodies demonstrating reduced level of LFA-1 expression. FIG. 10C: CD34$^+$ cells from the same patient after intensive chemotherapy (AT), which increases the levels of normal cells, were also stained with the same antibodies, demonstrating restoration of LFA-1 expression. SDF-1 failed to induce activation of LFA-1 binding to ICAM-1 on leukemic cells (data not shown). FIG. 10D: CD34$^+$ cells from the same CML patient, either newly diagnosed (ND) or after treatment with intensive chemotherapy (AT), were assayed for their migration potential to a gradient of SDF-1 in a transwell assay. Percent normal cells by fluorescent in situ hybridization (FISH) of non-migrating (NM) and migrating (M) are indicated.

DETAILED DESCRIPTION OF THE INVENTION

Figure 1A:
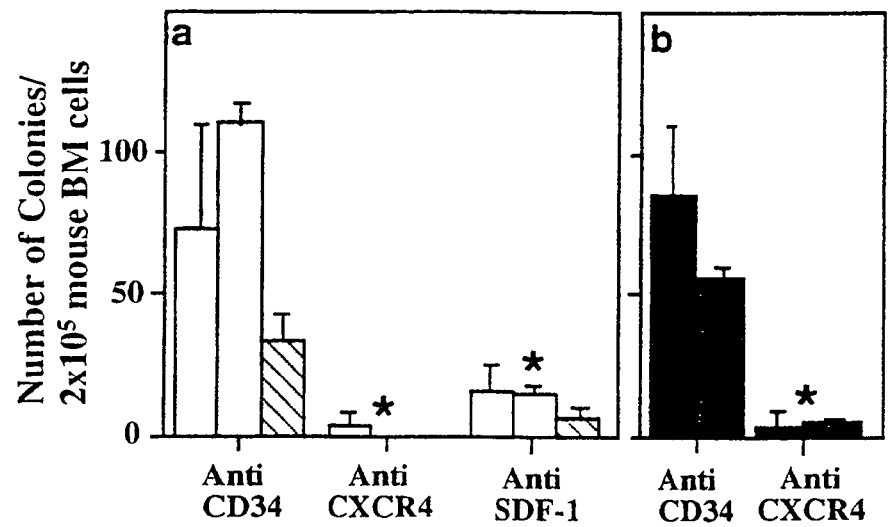
FIGS. 1A–1C show the effect of antibodies to CXCR4 and SDF-1 on engraftment of NOD/SCID mice bone marrow (BM) by human CD34$^+$ cells.

Functional in vivo assays for primitive human SCID repopulating cells that provide a means to measure the engraftment properties of various types of human hematopoietic cells, have been developed in recent years by us and by others (Lapidot et al., 1992; Larochelle et al., 1996; Cashman et al., 1997; Bhatia et al., 1998) Elucidation and characterization of processes that regulate migration of human hematopoietic stem/progenitor cells and their homing to the bone marrow permit to develop means for enhancing the incidence of stem cells with migration and engraftment potential.

According to the present invention, we identified the chemokine SDF-1 as a key mediator of migration and engraftment of human CD34$^+$CXCR4$^+$ and CD34$^-$CXCR4$^+$ cells to the bone marrow of immune deficient mice. This is the first assignment of a distinct in vivo function of SDF-1 using human cells. We further identified a functional internal hierarchy within the early population of CD34$^+$CD38$^{-/low}$ and CD34$^-$CD38$^{-/low}$ cells. In this population, a minority of the primitive cells that were CXCR4$^+$ and migrated to a gradient of SDF-1 in vitro, repopulated the murine bone marrow with SRC. Our data characterizes SRC as CD34$^+$CD38$^{-/low}$ CXCR4$^+$ and CD34$^-$CD38$^{-/low}$ CXCR4$^+$ cells with major stem cell properties. We thus redefine human SRC/stem cells as those with a CXCR4$^+$CD38$^{-/low}$ phenotype and with the potential to migrate to a gradient of SDF-1 and to engraft the murine bone marrow with high levels of myeloid and lymphoid cells.

Based on these findings, we suggest that in vivo there is a steady-state balance between a minority of CD34$^+$ and CD34$^-$ cells that express sufficient levels of CXCR4 and consequently migrate to SDF-1, with a majority of the cells that express low levels of CXCR4 or do not express the receptor at all and therefore cannot migrate. This balance may be controlled by cytokines such as SCF that upregulates CXCR4 expression as well as by SDF-1 that inhibits CXCR4 expression after migration. Interestingly, this balance is also maintained in the primitive population of CD34$^+$CD38$^-$ and CD34$^+$CD38$^{-/low}$ cells, which contain a higher fraction of CXCR4$^+$ migrating cells than the more differentiated CD34$^+$CD38$^+$ cells that were isolated from bone marrow or cord blood. The above balance may reflect the production of SDF-1 in the bone marrow which in turn controls the localization of stem cells and their progeny within the marrow microenvironment. Mobilization of CD34$^+$ cells from the bone marrow to the blood circulation by cytokine stimulation alters this balance, resulting in heterogeneous levels of CXCR4 expression.

SCF. an early acting cytokine with many hematopoeitc functions, has a membrane bound form expressed on stromal cells as well as a soluble form (Zsebo et al., 1990) According to the present invention, we demonstrate that prolonged stimulation of mobilized peripheral blood, cord blood and bone marrow CD34$^+$ cells with SCF significantly increases CXCR4 cell surface expression as well as migration and bone marrow engraftment, indicating that the population of migrating human SRC/stem cells can be expanded ex vivo by upregulating CXCR4 expression. Stimulation with SCF and/or other cytokines and/or stromal cells involved in maintenance, expansion and/or development of stem cells, as described herein, can be thus applied to improve human stem cell transplantation protocols. Furthermore, it makes possible to purge in vitro malignant cells in cases of disease that require autologous transplantation, provided that the malignant cells do not migrate to a gradient of SDF-1.

Kim and Broxmeyer (1998) have shown that SCF can increase the motility of CD34$^+$ cells and also that SCF has low chemotactic and chemokinetic activities on human CD34$^+$ cells. Okumura et al. (1996) showed that prolonged in vitro exposure to a gradient of SCF results in migration of murine stem cells. SCF was moreover found to synergize with SDF-1, resulting in significantly increased levels of migration by human CD34$^+$ cells to a mixture of these chemoattractants in vitro (Kim and Broxmeyer, 1998).

Adhesion molecules are involved in the interactions between CD34$^+$ cells and the extracellular matrix as well as between CD34$^+$ cells and stromal cells (Teixido and Anklesaria, 1992). These interactions are pivotal in the process of horning and engraftment. The involvement of SDF-1 in the rapid physiological shift from rolling behavior on endothelial cells lining the blood vessels to firm ICAM-1/LFA-1 dependent arrest of human CD4$^+$ T lymphocytes suggests a similar mechanism of action for SDF-1 in the control of migrating CD34/CXCR4$^+$ cells (Campbell et al., 1998). Indeed neutralizing antibodies to LFA-1 could prevent engraftment by human CD34$^+$ cells. We have also found that SDF-1 is capable of activating shear-resistant adhesion of CD34$^+$CXCR4$^+$ cells to ICAM-1. We also found that SDF-1 also induced binding of CD34$^+$ cells to fibronectin. Using a novel 3-dimensional (3-D) ECM-like gel, we found that directional migration of CD34$^+$CXCR4$^+$ cells toward a chemotactic gradient of SDF-1 was dependent on VLA-4 as well as on VLA-5. Furthermore, we showed in vivo that neutralizing antibodies to VLA-4 and VLA-5 blocked the migration and engraftment of SRC/stem cells in murine bone marrow. These findings indicate that VLA-4 and VLA-5 interactions between human CD34$^+$CXCR4$^+$ cells and the ECM are critical for migration of stem cells to the bone marrow and successful engraftment. Postmigration adhesion to stromal cells by activation of VLA-4 and VLA-5 could be mediated by other cytokines such as SCF.

Based on the results shown herein in the specification, we suggest the following model for homing and engraftment of human SRC/stem cells to the bone marrow: immature Lin$^-$ cells are recruited to specialized sites on the bone marrow vessel wall, possibly through roiling interactions on constitutively expressed endothelial selecting. Following rolling, Lin$^-$ CXCR4$^+$ cells are activated by SDF-1 secreted from bone marrow stromal cells. Activation with SDF-1 triggers LFA-1 to support firm adhesion to endothelial ICAM-1. Lin$^-$ cells which do not express sufficient levels of the chemokine receptor CXCR4 will detach from the endothelial layer and return to the blood stream. The arrested human stem/progenitor cells, in response to a gradient of SDF-1, will extravasate and migrate through the underlying extracellular matrix using their VLA-4 and VLA-5 integrin receptors for fibronectin. Migrating cells will eventually reach "stem cell niches" consisting of stromal cells presenting the proper set of adhesion molecules (e.g. VCAM-1, ICAM-1) and growth stimulatory factors.

According to the present invention, it is shown that migration, and therefore the engraftment potential of stem/progenitor cells from cord blood, bone marrow, and mobilized peripheral blood cells, is essential for efficient engraftment. It appears that both in vitro migration and homing and engraftment of human Lin-CD38$^{-/low}$ CXCR4$^+$ SRC/stem cells can be regulated and increased.

While most previous studies have demonstrated the importance of the proliferation and differentiation potential of stem cells as the major criteria for their developmental and repopulation status, the present invention shows that CXCR4 dependent migration to SDF-1 is crucial for bone marrow engraftment and repopulation. Thus the migration capacity of the stem cells measured by cell surface CXCR4 expression, level of migration to a chemotactic gradient of SDF-1 and level of engraftment by primitive human CD34$^+$CD38$^{-/low}$ and CD34$^-$CD38$^{-/low}$ cells, is a highly variable factor that plays an equally important role.

With regard to the important issue of stem cell self-renewal that can only be quantified by serial stem cell transplantations, the results according to the present invention indicate that at least part of the decline in repopulating stem cells is not necessarily due to accelerated differentiation, as previously thought, but rather to loss of the majority of stem cells with migration and engraftment potential which fail to engraft due to low levels or complete lack of cell surface CXCR4 expression.

According to the invention, it is shown that engraftment of NOD/SCID mice by human stem cells is dependent on the major integrins LFA-1, VLA-4, and VLA-5. Treatment of human cells with antibodies to either of these integrins prevented engraftment. Activation of CD34$^+$CXCR4$^+$ cells with SDF-1 led to firm LFA-1/ICAM-1 and VLA-4/VCAM-1 dependent adhesion and transendothelial migration. Furthermore, SDF-1 induced polarization and extravasation of CD34$^+$CXCR4$^+$ cells through the extracellular matrix underlining the endothelium was both VLA-4 and VLA-5 dependent. Our results demonstrate that repopulating human stem cells functionally express LFA-1, VLA-4 and VLA-5. We further suggest a novel approach to advance autologous transplantation by purging malignant cells with abnormal migration to SDF-1 or SDF-1-dependent integrin adhesion interactions.

Stem cell homing and engraftment is a multistep process, sharing some common features with the migration of leukocytes to inflammatory sites and horning of lymphocytes into lymph nodes. First, the transplanted human cells which migrate in the blood circulation must interact with the bone marrow vascular endothelial cells. This results in rolling which is followed by firm shear resistant adhesion to the vessel wall. These interactions are mediated through the coordinated action of adhesive molecules and activation processes triggered specifically by chemokines, such as SDF-1, and vascular ligands such as VCAM-1 and ICAM-1. Following arrest, stem cells polarize and extravasate through the endothelium into the extracellular compartment using VLA-4 and VLA-5 reaching stem cell niches within the different stromal cells.

SDF-1 rapidly activated the firm shear-resistant adhesion of human CD34$^+$CXCR4$^+$ cells to immobilized ICAM-1. Chemokine-mediated activation was highly specific as it was totally inhibited in the presence of the integrin inhibitor EDTA.

Following extravasation through the vascular endothelium, stem cells encounter the bone marrow extracellular matrix barriers. During bone marrow transplantation stem cells need to pass through the basal lamina which is composed of the ECM proteins: laminin, collagen and fibronectin. SDF-1 mediated interactions between migrating human CB CD34$^+$CXCR4$^+$ cells and the extracellular matrix were studied in vitro by monitoring the migratory properties of these cells through a 3-dimensional (3-D) ECM-like gel, reconstituted with a meshwork of laminin, collagen and fibronectin. This novel system allows for close examination of the random and directional migration of cells towards a newly generated chemoattractant source in real time. Most CD34$^+$ cells embedded in this gel remained spherical and failed to polarize or migrate in the absence of SDF-1. However, upon introduction of an SDF-1 gradient, 40% of the cells polarized in a time-dependent manner. As much as 30% of the cells migrated towards a gradient of SDF-1. The percentage of polarized and migrating CD34$^+$ cells in 3-D ECM-like gel correlated with the levels of CXCR4$^+$ expression on CB CD34$^+$ cells (about 50% positive cells FIG. 1) and with the frequency of cells migrating towards a gradient of SDF-1 (between 20–30%). SDF-1 induced polarization and directional migration of CD34$^+$CXCR4$^+$ cells in 3D ECM-like gels is dependent on both VLA-4 and VLA-5 integrins.

As described herein before, we have found that SDF-1 activates shear-resistant adhesion of normal CD34$^+$CXCR4$^+$ cells to ICAM-1. These results suggest that during the process of homing LFA-1/ICAM-1 interactions are essential. We have also demonstrated that the migration of CD34$^+$ cells through the extracellular matrix is both VLA-4 and VLA-5 dependent.

Based on our studies we suggest a further possible scenario for homing specific for human CD34$^+$ SRC/stem cells to the bone marrow. Transplanted human CD34$^+$CD38$^{-/low}$ CXCR4$^+$ SRC/stem cells that express LFA-1, VLA-4 and VLA-5, reach the bone marrow and are recruited to specific vascular sites which constitutively express E/P selectin, ICAM-1 and VCAM-1. Upon activation with endothelium expressing or presenting SDF-1, LFA-1 and VLA-4, are activated on rolling stem cells to support their firm adhesion to the vessel wall. In response to a gradient of SDF-1, the arrested human stem cells extravasate into the bone marrow ECM compartment (diapedesis) using LFA-1. In extravascular space, by using VLA-4 and VLA-5 for movement across fibronectin, the stem cells polarize and migrate through the basal lamina towards local gradients of SDF-1, produced by specialized stromal cells, orienting themselves through the different elements of the bone marrow microenvironment and into the "stem cell niches".

In summary, we have herein further identified repopulating human SRC/stem cells as functionally expressing the integrins LFA-1, VLA-4 and VLA-5, both for migratory and adhesion processes triggered by endothelial or stromal associated SDF-1. Furthermore, our in vitro and in vivo data suggest chemokine-dependent differential roles for these major integrins in the multistep process of migration, engraftment and retention of human SRC/stem cells in the murine bone marrow microenvironment.

The present invention further provides a functional animal model for in vivo examination of human hematopoietic cell engraftment in mice, which serves several purposes: a) Identification of chemokines and cytokines such as SDF-1 and SCF that mediate or regulate migration and bone marrow engraftment by immature human Lin cells, b) Quantitative measurement of the migration and bone marrow engraftment potential of human Lin$^-$CD38$^{-/low}$CXCR4$^+$ SRC with major stem cell properties; c) Characterization of key adhesion molecules such as LFA-1, VLA-4 and VLA-5 and identification of their specific roles in migration and engraftment; d) Development of ex vivo protocols for expansion of SRC/stem cells by treatment with specific cytokines that upregulate CXCR4 expression and increase their migration and engraftment potential or with stromal cells that increase their engraftment potential.

The findings of the present invention delineate key steps in the complex engraftment process and suggest upregulation of CXCR4 and/or adhesion to stromal cells in response to an adhesion-inducing agent as novel approaches to expand migrating CXCR4$^+$ stem cells for clinical transplantation.

The invention will now be illustrated by the following non-limiting Examples;

EXAMPLES

Materials and Methods (a) Cells: Human cord blood (CB) cells from full term deliveries, mobilized peripheral blood (MPB) and bone marrow (BM) cells from leftover clinical allogeneic harvests from healthy donors, were obtained after informed consent and used according to procedures approved by the Human Experimentation and Ethics Committees of the Weizmann Institute of Science (Rehovot, Israel). MPB cells were collected after 5 days of in vivo treatment with G-CSF and SCF. The blood samples were diluted 1:1 in phosphate-buffered-saline (PBS), supplemented with 1% fetal calf serum (FCS) (Bet Haemek, Israel). Low density mononuclear cells (MNC) were collected after standard separation on Ficoll-Paque (Pharmacia Biotech, Uppsala, Sweden), and washed in RPMI with 1% FCS. In all experiments, samples of the same initial cell pool were compared. Differences in the results are due to the different CD34$^+$ cell sources (CB, BM, MPB). Murine 14F1.1 pre-adipocyte stromal cells were kindly provided by Prof. D. Zipori (Weizmann Institute of Science, Israel).

Enrichment of human CD34$^+$ and CD34$^-$ cells: Enrichment of human CD34$^+$ cells from MNC was performed with a magnetic bead separation kit (MiniMacs, Miltney Biotec, Bergisch Goldbach, Germany) according to the manufacturers' instructions. The purity of the enriched CD34$^+$ cells was 60–85% or >98% when the cells were passed over one or two columns, respectively. Cells were used directly after enrichment as indicated or frozen in 90% FCS with 10% DMSO. The CD34$^-$ cells that did not bind to the magnetic beads were obtained using a StemSep kit (Stem Cell, Vancouver, Canada) according to the manufacturer's instructions.

(b) Reagents and antibodies: SDF-1, SCF, IL-3, IL-6, IL-15 and GM-CSF were purchased from R&D Systems (Minneapolis, Minn.). Bovine serum albumin (BSA), PMA, propidium iodide, HBSS, HEPES, methylcellulose, 2-mercaptoethanol (2ME), FITC-dextran (10 kDa) and Collagen type I (CO-I) were from Sigma (St. Louis, Mo., USA). Human serum albumin (HSA) was from Calbiochem (La Jolla, Calif.). Human fibronectin (FN) was from Chemicon International Inc. (Temecula, Calif.). Laminin (LN) was from Cellagen (ICN Pharmaceuticals Inc., CA). Erythropoietin (EPO) was from Orto BioTech (Don Mills, ON, Canada). ICAM-1-fc was a gift from Dr. R. Lobb (Biogen, Cambridge, Mass.).

The anti-CXCR4 mAb 12g5 (IagG2a) and purified anti-mouse CD16/CD32 (FcR) were purchased from Pharmingen (San Diego, Calif.). The anti-CXCR4 MBA171 mAb (IgG2a) and polyclonal anti-SDF-1 were from R&D Systems (Minneapolis, Minn.). The murine anti-human VLA-4 (CD49d; IgG1), anti-human VLA-5 (CD49e; IgG2A) and anti-human LFA-1 (CD11a) mAbs were from Serotec (Oxford, UK). The anti-CD34 (IgG1) conjugated to fluorescein isothiocyanate (anti-CD34 FITC) was from Becton Dickinson (Lincoln Park, N.J.), anti-CD38 conjugated to phycoerythrin (anti-CD38 PE), anti-CD19 PE, and anti-CD56 PE were from Coulter (Miami, Fla.), anti-CD45 FITC was from Immuno Quality Products (Groningen, Netherlands). Purified mouse IgG (Zymed, South San Francisco, Calif.) was used as a control Ab.

(c) Flow cytometry analysis: For the analysis of engrafted human cells in the murine bone marrow, bone marrow cells from both femurs, tibias, humerus and pelvis bones from each transplanted mouse were flushed with a syringe and 26 gauge needle. Single cell suspensions ($1 \times 10^6$ cells/ml) were washed with PBS supplemented with 1% FCS and 0.02% sodium azide, after lysis of red blood cells with ammonium chloride.

For immunostaining, $10^5$ cells were resuspended in staining buffer (PBS, 0.1% BSA, 0.02% sodium azide), incubated with 10 μg/ml (1:50) of purified anti-mouse CD16/CD32 (FcR) and 1% human plasma for 20 minutes at 4° C. Cells were then stained with human specific, direct labeled antibodies (with FITC or PE) and incubated for 30 minutes on ice. Non-specific isotype control antibodies (mouse IgG) were used in order to exclude false positive cells. Murine bone marrow cells from non-transplanted mice were used as negative control and human cells as positive control. Dead cells were gated out by staining with propidium iodide.

Human cells from engrafted mice were analyzed for immature cells by double staining with anti-CD34 FITC and anti-CD38 PE, and for the presence of human lymphoid and myeloid cells by immunostaining with anti-CD45 FITC, anti-CD19 PE and anti-CD56 PE. Control cells were incubated with anti-CD34 (IgG1, 10 μg per $2 \times 10^5$ cells).

The levels of CXCR4 expression on human CD34$^+$ cells were detected by double staining with anti-CXCR4 PE (12g5 mAb) together with anti-CD34 FITC. The levels of immature cells in the transwell migration assay were analyzed by staining with anti-CD34 FITC and anti-CD38 PE. The presence of human natural killer (NK) cells [that differentiated into mature CD56$^+$ cells after incubation with 100 ng/ml human SCF and 100 ng/ml human IL-15 for 10 days] in cultures from transplanted mice were detected with anti-CD56 PE and anti-CD45 FITC. After staining, cells were washed twice in the same buffer and analyzed by fluorescence-activated cell separation (FACS) (Becton Dickinson, Calif.), using CellQuest software (Becton Dickinson, Calif.).

(d) Cell sorting: Cell sorting was performed on a FACStar plus (Becton Dickinson, Calif.) as previously described (Larochelle et al., 1996). In brief, single cell suspensions of human CD34$^+$-enriched cells were labeled with anti-human CD34 FITC and anti-human CD38 PE monoclonal antibodies. The purity of sorted CD34$^+$CD38$^{-/low}$ and CD34$^+$CD38$^+$ cells was >99%.

(e) Liquid cultures: Human CD34$^+$-enriched cells were seeded in 24-well plates (Costar, MA) (0.2–$1 \times 10^6$ cells in 0.5 ml), containing either serum free media (IMDM, 2%

BSA, 20 µg/ml human insulin, 40 µg/ml human low density lipoprotein (LDL), 200 µg/ml transferrin, $10^{-4}$ M 2ME and 10 mM HEPES buffer) or RPMI, 10% FCS, and 1% BSA. In addition, various combinations of cytokines and chemokines were added as indicated. Serum-free cultures yielded similar results compared to cultures that contained RPMI, 10% FCS and 1% BSA. The cultures were incubated at 37° C. in a humidified atmosphere containing 5% $CO_2$.

(f) Colony assay: Semisolid progenitor cultures were performed as previously described (Lapidot et al., 1992). In brief, the cells were plated in 0.9% methylcellulose, 30% FCS, $5 \times 10^{-5}$ 2ME, 50 ng/ml SCF, 5 ng/ml IL-3, 5 ng/ml GM-CSF and 2 U/ml EPO. Bone marrow cells from transplanted mice were cultured under conditions selected for growth of human colonies only, by replacing 15% FCS with 15% human plasma Plating concentrations were: enriched $CD34^+$ cells—$3 \times 10^3$ cells/ml, bone marrow cells from transplanted mice—$200 \times 10^3$ cells/ml. The cultures were incubated at 37° C. in a humidified atmosphere containing 5% $CO_2$ and were scored 14 days later.

(g) Mice: NOD/SCID mice (NOD/LtSz $PrKdc^{scid}$/$PrKdc^{scid}$) (kindly provided by Dr. John Dick, with the approval of Dr. Leonard. Schultz, HSC Toronto, Ontario, Canada) and NOD/SCID β2-microglobulin-knock out mice (NOD/SCID β2M KO) (kindly provided by Dr. Leonard D. Shultz, Jackson Laboratories, Bar-Harbor, Me., U.S.A) were bred and maintained under defined flora conditions in intra-ventilated (HEPA filtered air) sterile micro isolator cages (Techniplast, Italy) at the Weizmann Institute of Science. All the experiments were approved by the Animal Care Committee of the Weizmann Institute. Mice, 8-week old, were irradiated with a sublethal dose of 375cGy-67cG/min. from a cobalt source prior to transplantation. Human $CD34^+$-enriched cells were injected into the tail vein of irradiated mice in 0.5 ml of RPMI with 10%. FCS. For in vivo blocking experiments, the cells were first preincubated with 10 µg/ml of anti-CXCR4 antibodies (MBA171 or 12g5 mAb), or with 10 µg/ml of anti-VLA-4, anti-VLA-5 and anti-LFA-1 antibodies, or with anti-human CD34 antibodies as negative control, for 30 minutes on ice. The cells were then washed and injected into mice. Alternatively, transplanted mice were intraperitoneally injected with anti-CXCR4 or anti SDF-1 antibodies, as indicated. Polyclonal anti-SDF-1 (10 µg per mouse) was injected intravenously with the cells ($2 \times 10^5$ cells per mouse) and 24 hours later injected again intraperitoneally. Mice were sacrificed after 14–45 days post-transplantation as indicated. Percent engraftment is indicated by the percent of human CD45 cells in the mouse bone marrow. The levels of engraftment were dependent on the injected cell dose, the duration of the experiment, and the source of human $CD34^+$ cells.

(h) Southern (DNA) blot analysis: The relative amounts of human cells in bone marrow of transplanted mice was determined by sacrificing the mice, extracting high-molecular weight DNA from their bone marrow and spleens with phenol/chloroform, digesting the DNA (5 µg) with EcoRI, subjecting to electrophoresis on 0.6% agarose gel, blotting onto a nylon membrane and hybridizing with p17H8, a human α-satellite probe specific for sequences on human chromosome 17, labeled with $^{32}P$. EcoRI digestion of human DNA produces a characteristic 2.7 kb band from human chromosome 17 visible by autoradiography. The percent of engraftment of human cells in the mouse bone marrow was measured by determining the intensity of the characteristic 2.7 kb human chromosome 17 band in the EcoRI digested DNA samples, using artificial human/mouse DNA mixtures of known proportions (0%, 0.1%, 1%, and 10% human DNA) as standards.

(i) Transwell migration assay (chemokines and chemotaxis assay): Chemotaxis experiments with human $CD34^+$ cells (>98% purity) were assayed by using Costar transwells (Cambridge, Mass., 6.5 mm/diameter, 5 mm/pore). One hundred microliters of chemotaxis buffer (RPMI 1640, 1% FCS) containing $2 \times 10^5$ $CD34^+$ cells were added in the upper chamber, and 0.6 ml of chemotaxis buffer both with or without different concentrations of SDF-1 were added to the bottom chamber. Cells migrating within 4–5 h to the bottom chamber of the transwell were counted for 30 seconds using the FACSort (Becton Dickinson). Percent in the results represent percent of initial $2 \times 10^5$ $CD34^+$ cells in the migrating and nonmigrating cell fractions.

(j) Controlled Detachment Adhesion Assay: Laminar flow adhesion assays were performed as previously described (Carr et al., 1996). In brief, the adhesion proteins (ICAM-1) were diluted in coating medium (PBS supplemented with 50 mM Tris pH 9.0) and adsorbed as 20 µl spots on polystyrene plates (a polystyrene 60×15 mm petri dish, Becton Dickinson, Lincoln Park, N.J.) for 2 h at 37° C. The plates were then washed three times with PBS and blocked with HSA (20 mg/ml in PBS) overnight at 4° C. The plates were assembled as the lower stage of a parallel plate laminar flow chamber and mounted on the stage of an inverted phase contrast microscope (Diaphot 300, Nikon Inc., Japan). All flow experiments were performed at 37° C., maintained by warming the microscope stage with heating lamps in a humidified atmosphere. For the adhesion assay, a suspension of $CD34^+$ cells in a binding buffer were perfused into the flow chamber and allowed to settle on the substrate coated with the adhesion protein for 1 min. at 37° C. Adherent cells which had accumulated in the field of view during a 45 sec perfusion period at a wall shear stress of 0.75 or 1 dyn.cm$^2$ were subjected to detachment by incremented flow. The wall shear stress was increased in 2 to 2.5-fold increments every 5 sec to generate controlled shear stresses on the wall. Shear stress was generated with an automated syringe pump (Harvard Apparatus, Natick, Mass.) attached to the outlet side of the flow chamber. The wall shear stress was increased step-wise by a programmed set of flow rates delivered by the syringe pump. Cells were visualized in a 20× objective of an inverted phase-contrast Diaphot Microscope (Nikon, Japan) and photographed with a long integration LIS-700 CCD video camera (Applitech, Holon, Israel), connected to a video recorder (AG-6730 S-VHS, Panasonic, Japan). The number of adherent cells resisting detachment by the elevated shear forces and remaining bound to the coated substrate at the end of each 5 sec interval of incremented shear, was determined after each interval by analysis of videotaped cell images, and was expressed relative to the number of cells that accumulated on the adhesion protein at the end of the first 45 sec accumulation period. To test the effects of SDF-1 or PMA, cells were suspended in binding medium containing SDF-1 or PMA, seconds before being perfused into the chamber. All adhesion experiments were performed at least three times on multiple test fields that contained 50–100 cells/field.

(k) Real-time tracking of $CD34^+$ cell migration in ECM-like 3D gels: Purified (>98%) CB $CD34^+$ cells were suspended in a 5 ml drop of a gel-like medium consisting of collagen type I (CO-I), laminin and fibronectin (FN), in RPMI (at final concentrations of 1.8 mg/ml; 6 and 2.5 mg/ml, respectively). A second drop without cells was placed 1.5 mm from drop I. An SDF-1 depot was created in a third gel-like drop supplemented with SDF-1 (500 ng/ml), placed 1.5 mm downstream of drop II and 3–5 mm from drop I. Once the three gelatinous drops started to polymerize, the drops were gently connected with a fine needle to form a continuous 3D gel and cell migration within this gel was tracked by time-lapse videomicroscopy. Cell images were visualized as described above and videotaped on a time-lapse video recorder (AG-6730 S-VHS, Panasonic) at 25 frames per min.

Cell locomotion was analyzed manually from played-back video segments. CD34$^+$ cell positions in a representative field of view were tracked for 60–90 min. Time zero (t=0) was set according to the time at which the cells located at the edge of the field closest to the chemoattractant source started to spread and polarize, in response to the diffused chemoattractant. In representative experiments, FITC-dextran (10 kDa) was introduced into drop I and used as a marker to monitor the rate of chemokine diffusion within the connected drops. Cellular movements were assigned as follows: stationary cells with polarized morphology (polarized), motile cells that moved randomly in the gel or in a direction away from the chemoattractant (randomly migrating cells), and cells that migrated towards the source of the chemoattractant (directionally moving cells). The proportions of polarized, non-motile, randomly migrating, and directionally migrating cells within the entire population of cells in the field were determined for six intervals within the time of 60–90 min of tracking. The role of specific β1 integrins in human CD34$^+$ cell migration was examined by preincubating (10 min, 4° C.) CD34$^+$ cells (10$^6$/ml) in a 200 ml RPMI mixture containing 1% BSA and 5 μg of a control isotype-matching mAb, and then incubating (20 min, 4° C.) with specific anti-VLA-4 and anti-VLA-5 mAbs. Subsequently the CD34$^+$ cells were extensively washed and added to the 3D gels. When injected into mice, CD34$^+$ cells (60–85% purity) (2×10$^5$/mouse) were preincubated (20 min, 4° C.) with murine mAb to the human adhesion antigens of the β1-integrins VLA-4 and VLA-5 and the β2-integrin LFA-1.

EXAMPLES

Example 1

Anti SDF-1 and Anti-CXCR4 Antibodies Inhibit Homing of Human CD34$^+$ Cells into the Murine Bone Marrow To examine the in vivo role of SDF-1 and its receptor CXCR4 in migration and engraftment/repopulation by human SRCs, CD34$^+$-enriched cord blood cells were treated either with two different monoclonal antibodies to CXCR4 or with control anti-CD34 before transplantation of NOD/SCID mice.

Human cord blood CD34$^+$ cells were treated for 30 minutes with two alternative mono clonal antibodies to CXCR4 (12g5 or MBA171, 10 μg per 2×10$^5$ cells) or with anti-CD34 (IgG1, 10 μg per 2×10$^5$ cells) as a control, and the treated cells were transplanted into NOD/SCID mice (2×10$^5$ cells/mouse). Alternatively, polyclonal anti-SDF-1 (10 μg per mouse) was coinjected intravenously with the cells (2×10$^5$ cells/mouse) and 24 hours later reinjected again intraperitoneally. The mice were sacrificed after two weeks and the levels of human progenitor cells were quantified by human-specific semi-solid colony-forming assays. The following cell types were counted: CFU-GM (white bars), BFU-E (dashed bars), and multilineage CFU-GE (striped bars) (FIG. 1A, panel a).

The experiment was repeated with hematopoietic cells from different human sources: human bone marrow (black bars) or mobilized peripheral blood (stippled bars) CD34$^+$ cells were treated with the indicated antibodies and transplanted into NOD/SCID mice (FIG. 1A, panel b). Total human progenitors were quantified after one month as described above for cord blood cells.

As shown in FIG. 1A, panel a, only anti-CXCR4, but not anti-CD34, reduced engraftment. Antibodies to SDF-1 coinjected with human CD34$^+$-cord blood cells and readministered after 24 hours significantly reduced the level of engraftment. Similar treatment of human CD34$^+$-enriched cells from adult bone marrow or mobilized peripheral blood also resulted in inhibition of engraftment (FIG. 1A, panel b).

Figure 1B:
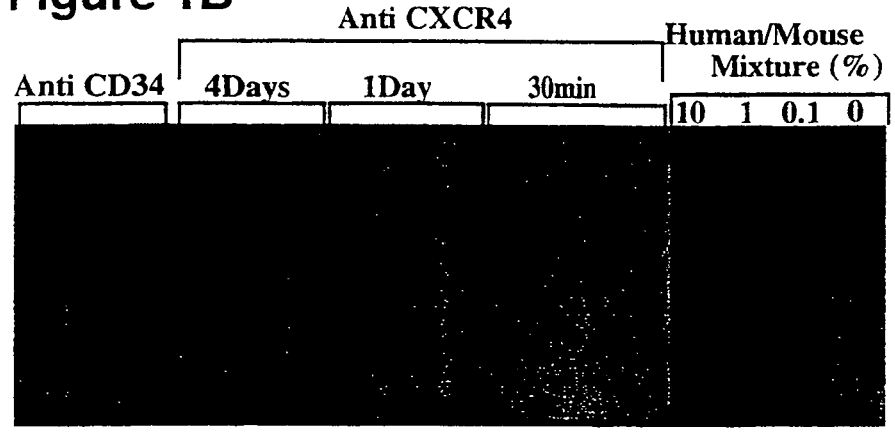

Cord blood CD34$^+$ cells were transplanted into NOD/SCID mice, followed by injection of anti-CXCR4 12g5 monoclonal antibody at the indicated times in FIG. 1B (30 min, 1 day and 4 days) after transplantation. Control cells were incubated with anti-CD34. After two weeks, mice were sacrificed and bone marrow was assayed by Southern blot for human DNA with the human-specific α satellite probe p17H8. Each lane in FIG. 1B represents DNA extracted from the bone marrow of one transplanted mouse. As shown in FIG. 1B, the kinetic experiments in which anti-CXCR4 antibodies were administered at varying points in time after transplantation revealed that the first 24 hours were critical to the engraftment process. Antibodies administered intraperitoneally 30 min after transplantation blocked engraftment. Antibodies administered 24 hours later reduced engraftment, although less effectively and were completely ineffective when administered 4 days after transplantation.

Figure 1C:
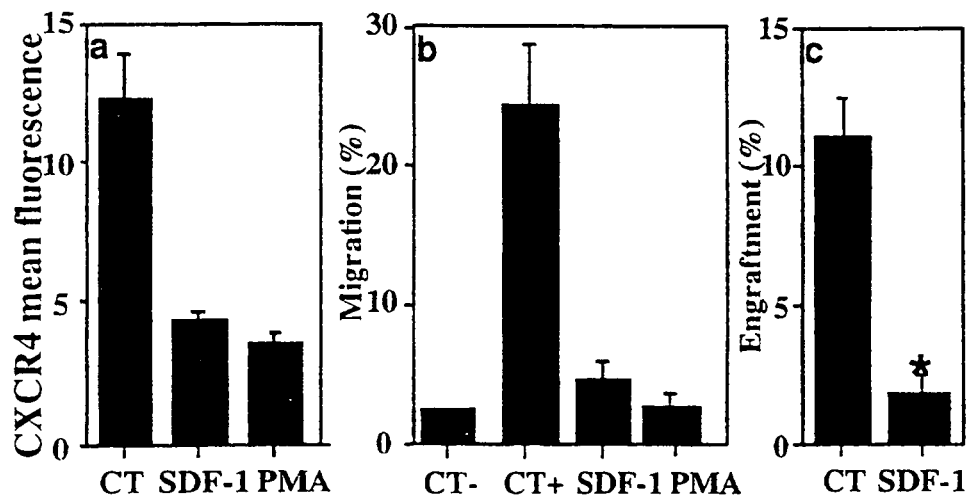

SDF-1 and PMA were reported to cause internalization and down-regulation of CXCR4 surface expression on human CD4$^+$ T cells (Signoret et al., 1997). To study the effects of SDF-1 desensitization and CXCR4 down-regulation on the ability of human CD34$^+$ cells to migrate and engraft NOD/SCID mice, cord blood CD34$^+$ cells were either not treated (CT) or were treated for 24 hours with high doses of SDF-1 (2 μg/ml) or PMA (100 ng/ml) (FIG. 1C). Cells were subsequently washed and tested for CXCR4 expression by immunostaining with anti-CXCR4 PE and anti-CD34 FITC, and for migration to SDF-1 in a transwell assay by immunostaining with anti-CD34 FITC and anti-CD38 PE. After staining, cells were washed twice n the same buffer and analyzed by FACS.

Both SDF-1 and PMA reduced cell surface expression of CXCR4 on human CD34$^+$ cells within 30 minutes of addition (data not shown). As shown in FIG. 1C, prolonged CXCR4 desensitization and down-regulation prevented engraftment of NOD/SCID mice. FIG. 1C, panel a, shows CXCR4 surface expression of CD34$^+$ cells immunostained for CXCR4 and shows that treatment of CD34$^+$ cells with PMA or SDF-1 reduced CXCR4 cell surface expression. FIG. 1C, panel b, shows percent background migration of CD34$^+$ cells in response to SDF-1 (125 ng/ml) in a transwell migration assay of untreated control cells without SDF-1 (CT−) or with SDF-1 (CT+), and migration to SDF-1 of cells treated with SDF-1 and PMA, and shows that such such treatment abolished the migration of CD34$^+$ cells in response to SDF-1, without affecting the ability of the cells to form colonies in vitro (data not shown). FIG. 1C, panel c, shows the percent of human cells in NOD/SCID mice, 1 month after transplantation (2×10$^5$ cells/mouse), as determined by FACS analysis by immunostaining with monoclonal antibodies to human CD45, and shows that prolonged (24 hours) treatment of CD34$^+$ cells with high doses of SDF-1 significantly blocked the engraftment of transplanted NOD/SCID mice. Thus, SDF-1 probably affects SRC engraftment by mediating chemotaxis to the bone marrow, linking migration to SDF-1 in vitro to human stem cell function in vivo.

Example 2

SDF-1 Preferentially Induces Migration and Engraftment of $CD34^+CD38^{-/low}$ $CXCR4^+$ Cells The results above lead us to the conclusion that the antibodies to CXCR4, or SDF-1 desensitization and CXCR4 internalization interfered with one or several steps in the engraftment process. We therefore proceeded to analyze the target cells for these antibodies and the mechanism by which the chemokine SDF-1 and its receptor CXCR4 mediate hemopoietic repopulation.

The migration potential of human $CD34^+$ cells was tested in vitro in a transwell migration assay in response to a gradient of SDF-1. FIG. 2 shows that SDF-1 induces the migration of SCID repopulating cells (SRCs).

FIG. 2A, panel a, shows migration of $CD34^+$ cells in response to a SDF-1 gradient. The transwell migration assay was performed with human $CD34^+$ cells from cord blood (C), bone marrow (B), or mobilized peripheral blood (MB) cells added to the upper chamber and SDF-1 to the bottom chamber (125 ng/ml). The control experiment (CT) was carried out without SDF-1 in the bottom chamber. The percent of human cells was quantified. Consistent with previous studies (Aiuti et al., 1997), we also found that 20 to 25% of cord blood and bone marrow $CD34^+$ cells migrated in response to a chemotactic gradient of SDF-1 in all donors tested. Migration of mobilized peripheral blood $CD34^+$ cells from multiple donors to migrate in response to SDF-1 was variable (between 8% to 60%), suggesting the involvement of SDF-1 in the mobilization process.

Similar results were obtained when human $Lin^-$ cord blood or bone marrow or MPB cells were used (data not shown). This migration was also dependent on CXCR4 expression since anti-CXCR4 antibodies inhibited this migration (data not shown).

The SDF-1 migrating (M) and nonmigrating (NM) cells were assayed for progenitors. The percent of human cells was quantified. As shown in FIG. 2A, panel b, the migrating (M) and nonmigrating (NM) $CD34^+$ cells did not differ in the incidence of progenitor cells, as determined by in vitro colony assays; however, the engraftment potential of the migrating and nonmigrating $CD34^+$ cells was different.

Equal numbers of SDF-1 migrating (M) and nonmigrating (NM) cells from the upper and lower chambers were washed and transplanted into NOD/SCID or $\beta_2$-microglobulin knockout NOD/SCID mice ($3\times10^4$ cells per mouse). The percent of human cells was quantified. As shown in FIG. 2A, panel c, whereas mice transplanted with nonmigrating (NM) cells from the upper chamber were poorly engrafted, mice transplanted with migrating (M) cells were significantly better engrafted. The low concentrations of SDF-1 and the limited exposure time caused only a transient decrease of CXCR4 expression that did not prevent engraftment. These results are further evidence for the link between in vitro motility to SDF-1 and in vivo stem cell function.

FIG. 2A, panels CB and BM, show that SDF-1 preferentially induces migration of $CD34^+CD38^{-/low}CXCR4^+$ cells. Surface expression of CD38 on cord blood (panel CB) and bone marrow (panel BM) $CD34^+$ cells labeled with anti-human CD34 FITC and anti-human CD38 PE was analyzed by flow cytometry on SDF-1 migrating (M) or nonmigrating (NM) cells. R gates $CD34^+CD38^-$ cells. Although only 20 to 25% of cord blood $CD34^+$ cells migrated toward SDF-1, this population contained a significantly higher percentage of primitive $CD34^+CD38^-$ cells than did nonmigrating cells left in the upper chamber (FIG. 2A, panel CB). In $CD34^+$ cells from human bone marrow, the proportion of immature $CD34^+CD38^{-/low}$ cells migrating to SDF-1 was larger than in cord blood (FIG. 2A, panel BM). Nevertheless, most cord blood $CD34^+CD38^-$ cells (60%) did not migrate to SDF-1, demonstrating that $CD34^+CD38^-$ cells are a heterogeneous population composed mostly of nonmigrating cells.

Sorted $CD34^+CD38^{-/low}$ cord blood cells from different donors were evaluated for their ability to migrate toward a chemotactic gradient of SDF-1 in vitro on the basis of surface CXCR4 expression and for their content of SRCs in vivo. Only 26% (±7%) of $CD34^+CD38^{-/low}$ cells from eight different donors migrated to a gradient of SDF-1 in the tanswell migration assay.

Figure 2B:
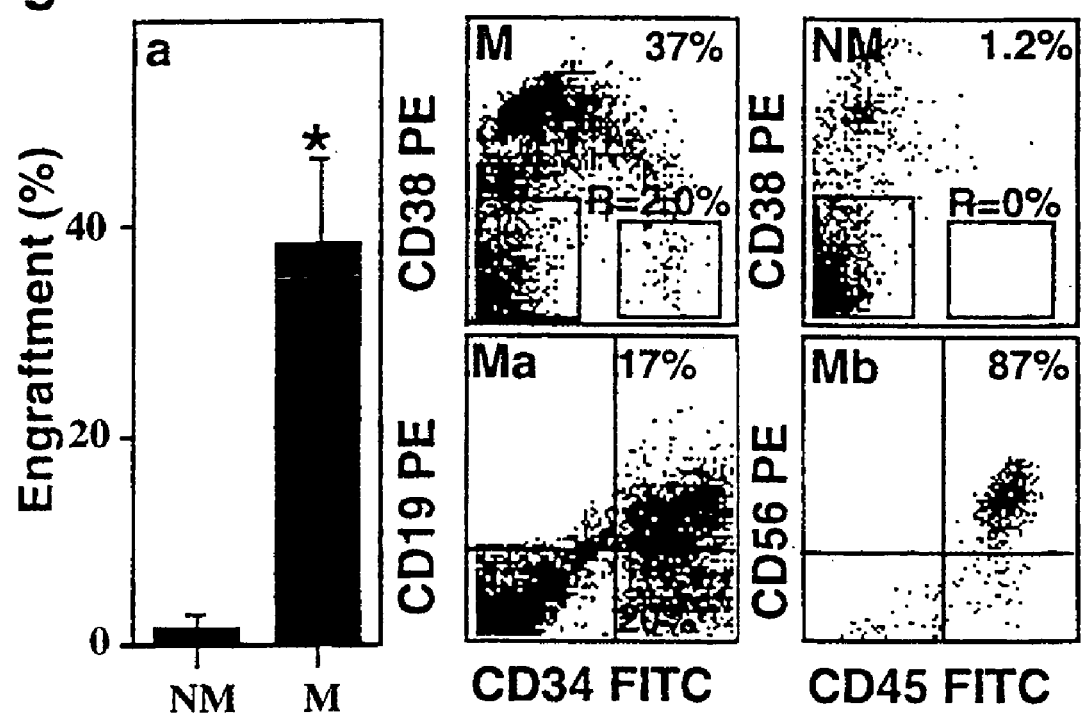

FIG. 2B shows sorted cord blood $CD34^+CD38^{-/low}$ cells: in panel a, SDF-1 migrating (M) or nonmigrating (NM) cells were transplanted into NOD/SCID mice ($3\times10^4$ cells per mouse). After 6 weeks, percent of engraftment was quantified and phenotype analysis of engrafted M and NM cells was performed. The presence of human $lympCD45^+CD19^+$ pre-B cells and progenitors for human $CD45^+CD56^+$ natural killer cells are shown in panels Ma and Mb, respectively. In a typical experiment, transplantation of migrating $CD34^+CD38^{-/low}$ cells into NOD/SCID mice resulted in high levels of multilineage engraftment. This was reflected in the engraftment of primitive $CD34^+CD38^-$ cells (FIG. 2B, panel M) and lymphoid (FIG. 2B, panels Ma and Mb), and myeloid colony-forming cells. In contrast, little engraftment was observed with nonmigrating $CXCR4^{-/low}$ cells (FIG. 2B, panel NM). Thus, the $CD34^+CD38^{-/low}$ $CXCR4^+$ migrating cell population, representing less than one-third of all $CD34^+CD38^{-/low}$ cells, engrafts the murine bone marrow with SRCs.

Example 3

Potentiation of the In Vitro Migration of MPB and Cord Blood $CD34^+$ Cells Toward a Chemotactic Gradient of SDF-1 and Enhancement of Their Engraftment Potential by SCF alone or Together with IL-6

Kim and Broxmeyer (1998) have demonstrated that SCF attracts $CD34^+$ cells, increases their motility and synergizes with SDF-1, increasing migration to both cytokines in vitro.

Figure 3A:
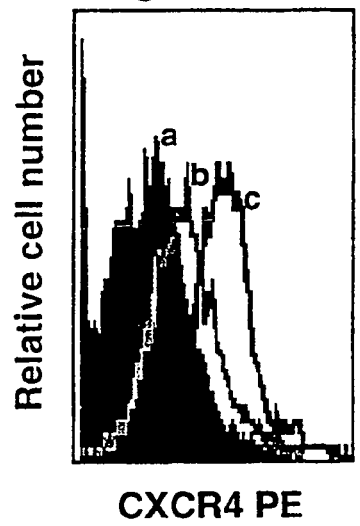
FIGS. 3A–3D show that SCF potentiates CXCR4 expression, cell migration, and SRC engraftment.
Figure 3B:
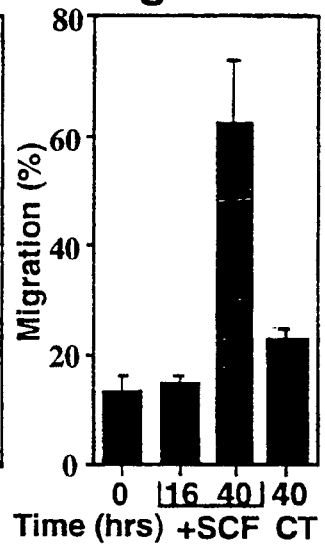
Figure 3C:
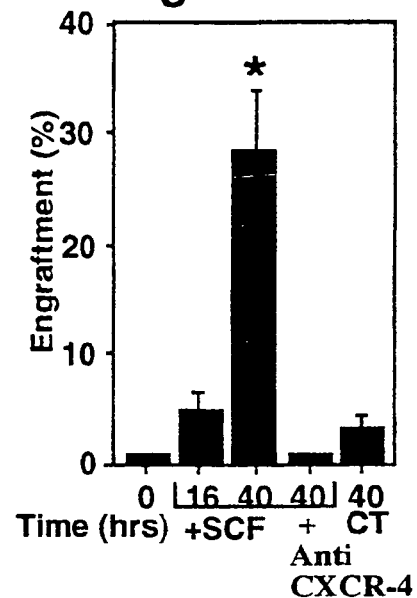
Figure 3D:
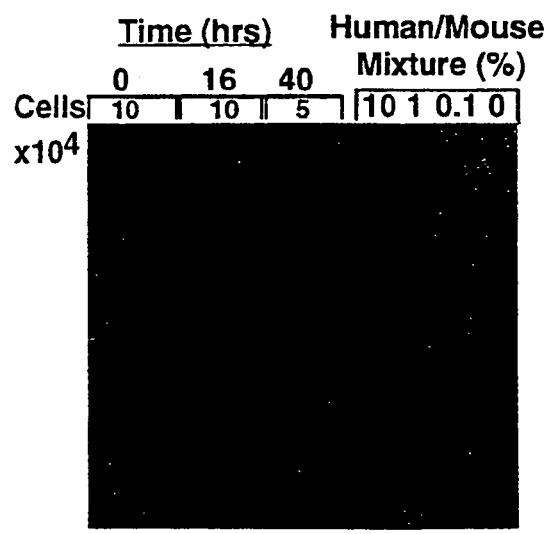

In order to see whether SCF potentiates CXCR4 expression, cell migration and SRC engraftment, human MPB $CD34^+$ cells were stained with control antibody (curve a) or with anti-CXCR4 monoclonal antibody before (curve b) or after (curve c) 40 hours of treatment with SCF (50 ng/ml), and assayed for surface expression of CXCR4 by immunostaining (FIG. 3A). SDF-1 transwell migration was carried out with untreated (0), SCF-treated (16 and 40 hours), or control cells cultured for 40 hours without SCF (CT). Data are average ±SE of 3 experiments (FIG. 3B). The percent of engraftment in NOD/SCID mice of human transplanted with $2\times10^5$ MPB $CD34^+$ cells was quantified before (0) or after 16 or 40 hours of exposure to SCF (50 ng/ml) and 40 hours of exposure to SCF followed by incubation with anti-CXCR4 (+ anti CXCR4). Control cells (CT) as in FIG. 3B. Percent of engraftment was quantified (FIG. 3C). The cells were exposed as above. At time 0 and after 16 hours $1\times10^5$ cells per mouse were transplanted, and after 40 hours half the amount of cells (0.5×10⁵ cells) per mouse were transplanted. Human engraftment was quantified after 1 month by Southern blot analysis (FIG. 3D).

Unexpectedly, prolonged (24- to 48-hour) stimulation of MPB CD34⁺ cells with SCF resulted in increased CXCR4 expression (FIG. 3A), enhanced migration toward SDF-1 (FIG. 3B), and enhanced engraftment potential dependent on the exposure time to SCF (FIG. 3C). Engraftment potential was similarly increased when only half the cell number was injected after 40 hours of SCF treatment, compared with 16 hours of exposure or untreated cells transplanted at time 0 (FIG. 3D). Thus, enhanced CXCR4-dependent migration to SDF-1 was accompanied by an increase in the SRC fraction. Incubation of SCF-stimulated, MPB CD34⁺ cells with anti-CXCR4 antibodies prevented engraftment (FIG. 3C).

Figure 4A:
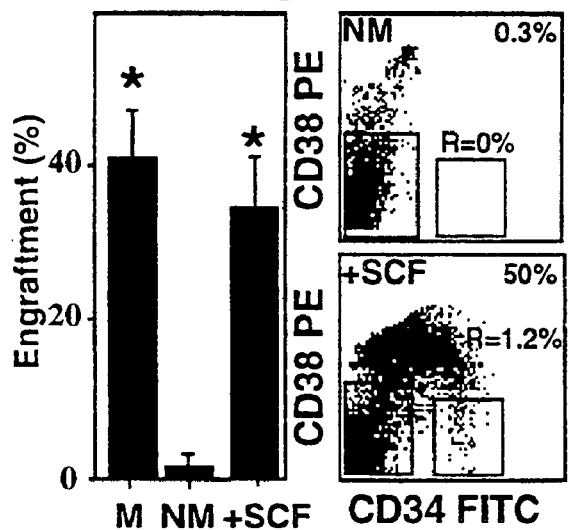
FIGS. 4A–4C show increase in SRCs and of stem cell self-renewal by up-regulation of CXCR4 expression.
Figure 4B:
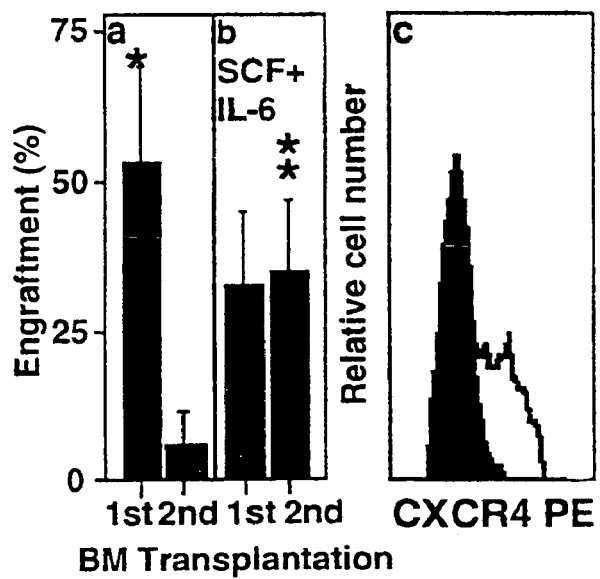
Figure 4C:
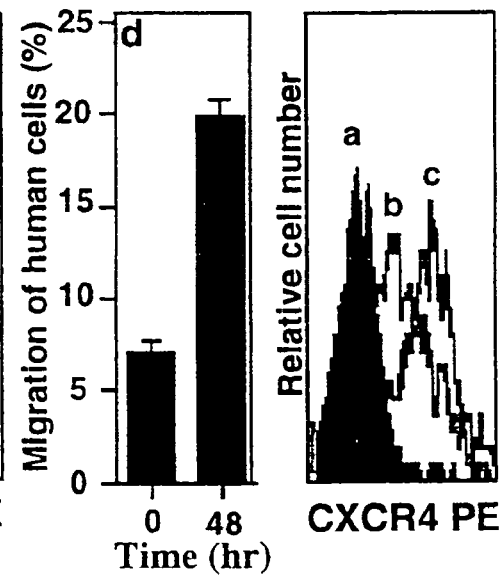

To test whether there is an increase in SRCs and of stem cell self-renewal by up-regulation of CXCR4 expression, sorted CD34⁺CD38$^{-/low}$ cord blood cells migrating toward SDF-1 were transplanted into NOD/SCID mice (3×10⁴ cells per mouse) (M). Sorted Nonmigrating CD34⁺CD38$^{-/low}$ CXCR4$^{-/low}$ cord blood cells toward SDF-1 were either transplanted directly (NM) or treated with SCF for 48 hours and then injected (+SCF). After 6 weeks, engraftment levels were quantified (FIG. 4A). Then BM cells from mice transplanted 4 to 6 weeks before with human cord blood CD34⁺ cells (FIG. 4B, panels a and b) were retransplanted untreated (2$^{nd}$ in panel a) or after SCF and IL-6 treatment for 48 hours (panel b) into secondary $\beta_2$-microglobulin knock-out NOD/SCID mice. FIG. 4B, panels c and d show human CXCR4 expression on cord blood cells from transplanted mice immediately labeled (solid) or after 48 hours treatment with SCF and IL-6 (open), and SDF-1 migration of cord blood cells from the marrow of transplanted mice before and after treatment with SCF and IL-6 for 48 hours, respectively. The cord blood CD34⁺ cells were stained with control antibody or antibody to CXCR4 after a 48-hour exposure to SCF or to a mixture of SCF/IL-6 (curve c), and the percent of engraftment was quantified (FIG. 4C).

Whereas nontreated cells had low engraftment efficiency (FIG. 4A), SCF treatment resulted in increased migration toward SDF-1 and properties that were similar to those of the original migrating fraction (M) (FIG. 4A).

Self-renewal of stem cells can only be determined by their ability to also repopulate secondary transplanted recipients with high numbers of both myeloid and lymphoid cells. Consistent with previous studies, secondary transplanted mice that received untreated human cells showed little engraftment (FIG. 413, panel a) (Spangrude et al., 1995). Human IL-6 synergizing with SCF induced high levels of CXCR4 expression on CD34⁺ cord blood cells (FIG. 4C). Incubation of bone marrow cells from primary transplanted mice with SCF and IL-6 for 48 hours resulted in upregulation of surface CXCR4 expression (FIG. 4B, panel c) and increased migration of human progenitor cells to SDF-1 in vitro (FIG. 4B, panel d). Transplantation of similar numbers of human cells from the bone marrow of primary transplanted mice after treatment with these cytokines resulted in higher engraftment levels in secondary transplanted mice compared with mice transplanted with untreated cells (FIG. 4B, panel b versus panel a). Thus, by upregulating surface CXCR4 expression on primitive cells, the population of self-renewing CD34⁺CD38$^{-/low}$ SRC stem cells could be increased.

Example 4

Activation of CD34⁺ Cells with SDF-1, in the Presence of Stromal Cells, Increase the Potential of the Cells to Engraft in the Bone Marrow of NOD/SCID Mice The role of chemokines such as SDF-1 in determining the migration and localization of human hematopoietic progenitors within the extravascular space is unknown. To study the role of SDF-1 in regulating the interactions between human stem cells and the bone marrow stroma, we used murine 14F1.1 pre-adipocyte stromal cells and human primary stromal cells (data not shown).

The migration and engraftment properties of human cord blood CD34⁺ cells was compared using transwells with a gradient of SDF-1 and either bare filters (FIG. 5, black columns) or transwells with filters coated with the 14F1.1 stromal cells (2×10⁴ cells/well) and grown for 48 hours (FIG. 5, striped columns). The trans-stromal migration assay was performed without (−) and with (+) a gradient of SDF-1.

FIGS. 5A–5B show that SDF-1 stimulates the adhesion and trans-stromal migration of CD34⁺ progenitors and increases the number of SRCs. As shown in FIG. 5A, SDF-1 induced the adhesion of the human CB CD34⁺ progenitor cells to 14F1.1 stromal cells (FIG. 5A, right panel: Bound to Stroma). SDF-1 also induced the migration of the cells through the stromal layer and in both transwells similar percentage of CD34⁺ cells migrated toward the lower chambers and similar background migration was also observed in the lower chambers (FIG. 5A, middle panel: Down, Down+ Stroma). In the upper chamber uncoated with the stromal cells, most of the nonmigrating cells were found (FIG. 5A, left panel: UP). However, in the upper chamber coated with stromal cells, a reduced number of cells were found both in the unstimulated and in the SDF-1-stimulated transwells, the number of cells being more reduced in the presence of SDF-1 (FIG. 5A, left panel: UP+Stroma).

The cells that migrated into the lower chambers and the nonmigrating cells that remained in the upper chambers of both stroma-coated and -uncoated transwells were transplanted into NOD/SCID mice. As shown in FIG. 5B, similar engraftment percentages were found for the nonmigrating cells (FIG. 5B, left panel: UP) and for the migrating cells (FIG. 5B, middle panel: Down) when the migration assay was performed in the presence (+) or in absence (−) of stromal cells. However, low levels of engraftment resulted when cells collected from the upper chambers were injected into NOD/SCID mice (FIG. 5B, left panel: UP). When the CD34⁺ cells that adhered to the stromal cells (see FIG. 5A, Bound to Stroma) were coinjected into the NOD/SCID with stromal cells, these CD34⁺ cells engrafted the bone marrow with higher percentage of human SRCs (FIG. 5B, right panel: Bound to Stroma), indicating that costimulation of the CD34⁺ cells by SDF-1 and stroma, improved their levels of engraftment into the bone marrow of the NOD/SCID mice.

According to this example, migration of human CD34⁺ cells to SDF-1 across bare filters or across filters coated with stromal cells, resulted in 25% and 20–25%, respectively, of the cells migrating to SDF-1 in the lower chamber within 4 hours. These migrating cells contained human stem cells that engrafted and repopulated transplanted NOD/SCID mice with high levels of multilineage lymphoid and myeloid human cells. In addition, 50% of the human CD34⁺ cells adhered to the stromal cells within the 4-hour migration assay and this population also contained stem cells suitable for engraftment as the migrating cells. In this way, it is possible to increase the percent of stem cells suitable for engraftment from about 25% to 75% (25% migrating CXCR4$^+$ cells and 50% adhering CXCR4$^{low}$ cells).

Example 5

SDF-1 Induces Firm LFA-1 Mediated Adhesion of CD34$^+$ CXCR4$^+$ Cells to ICAM-1

In order to further understand the mechanism by which SDF-1 regulates migration and engraftment, the direct effect of SDF-1 on the ability of both β1 and β2 integrins to develop firm adhesion of cord blood CD34$^+$ cells to ICAM-1 and fibronectin (FN) was tested. Integrin-dependent adhesion assays were performed using a parallel-plate flow chamber, which simulates blood flow and allows the application of both weak and strong detaching forces on adherent cells as described in Materials and Methods.

Highly purified human cord blood CD34$^+$ cells (2×10$^6$ cells/ml, purity >98%) treated briefly with 3 μg/ml SDF-1 or 100 ng/ml PMA, or left untreated, were suspended in a binding buffer (Hank's balanced salt solution (HBSS) containing 10 mM HEPES pH 7.4, 1 mM Mg$^{2+}$, 2 mM Ca$^{2+}$, and 2 μg/ml HSA), perfused into a parallel plate flow chamber and allowed to bind for 1 minute at 37° C. on substrate coated with immobilized ICAM-1 (ICAM-1-Fc fusion protein immobilized on protein A) in stasis (FIG. 6). [Protein A (20 μg/ml in coating medium) was spotted onto a polystyrene plate, and the substrate was blocked with 2% HSA in PBS. The protein A substrate was overlaid overnight at 4° C. with COS(COS cells transfected with cDNA of the fusion protein) supernatant containing 1–2 μg/ml of the fusion protein. The substrate was washed 5 times with PBS and blocked with 2% HSA in PBS prior to use]. The cells were then subjected to incremented shear flow (starting from 1 dyn/cm$^2$ and increasing the flow by step-wise increments every 5 seconds) which generated increasing detaching forces on the adherent cells.

As shown in FIG. 6, SDF-1 (black diamonds) rapidly activated the firm shear-resistant adhesion of CD34$^+$ CXCR4$^+$ cells to immobilized ICAM-1, the major LFA-1 ligand. This chemokine-mediated activation was almost as powerful as activation with the nonphysiological integrin agonist PMA (circles), and was integrin-dependent as it was totally inhibited by the addition of EDTA to SDF-1 (triangles). Upon initiation of flow, all cells detached immediately from control substrates coated with HSA or protein A (data not shown).

Example 6

Directional Migration of CD34$^+$ CXCR4$^+$ Cells Towards a Chemotactic Gradient of SDF-1 is Dependent on Both VLA-4 and VLA-5

Adhesion molecules are involved in the interactions between CD34$^+$ cells and bone marrow ECM as well as between CD34$^+$ cells and stromal cells (Teixido and Anklesaria, 1992). We studied the migratory properties of cord blood CD34$^+$ cells through a 3-dimensional (3-D) ECM-like gel, reconstituted with a meshwork of collagen, FN and laminin, to which an SDF-1 gradient was introduced. This novel system allows for the close examination of the random and directional migration of cells towards a newly generated chemoattractant source in real time. Most CD34$^+$ cells embedded in this gel remained spherical and failed to polarize or migrate in the absence of SDF-1 (FIG. 7A).

However, upon introduction of an SDF-1 gradient, 40%–50% of the cells polarized in a time dependent manner (FIG. 7A) and as much as 30% of the cells migrated toward a gradient of SDF-1 (FIG. 7B). Polarization and movement correlated with the level of surface CXCR4 expression on CD34$^+$ cells and with their transmigration capacity along a gradient of soluble SDF-1 (data not shown). Although SDF-1 did not mediate VLA-4 and VLA-5 adhesion, SDF-1-induced polarization and directional movement in ECM-like gels seem to be greatly dependent on VLA-4 and VLA-5, as observed in the inhibition of these processes by neutralizing antibodies to each of these integrins (FIGS. 7A, 7B).

To further determine the in vivo roles of LFA-1, VLA-4, and VLA-5 in migration and engraftment of human SRC, CD34$^+$ cord blood cells were pretreated with antibodies against one of the above integrins or as a control with anti-CD34 antibodies. As expected, anti-LFA-1, anti-VLA-4, and anti-VLA-5 antibodies all blocked the engraftment of CD34$^+$ cells into the mouse bone marrow, while control anti-CD34 antibodies did not (FIG. 7C). Our in vitro and in vivo results suggest a crucial role for integrins in the multistep process of migration and engraftment by human SRCs.

The above observations demonstrate the critical role of LFA-1, VLA-4 and VLA-5 in the migration and engraftment process.

Example 7

Preconditioning by Irradiation Increases SDF-1 Production in NOD/SCID Mice BM and Enhances Efficiency of BM Transplantation Irradiation of mice before transplantation with hematopoietic stem cells of human origin is essential for successful BM transplantation). However the mechanisms controlling this phenomena are not well understood. In this example, we have tested the possibility that, by irradiation, SDF-1 levels are upregulated, therefore affecting the engraftment and repopulation of the BM.

Figure 8A:
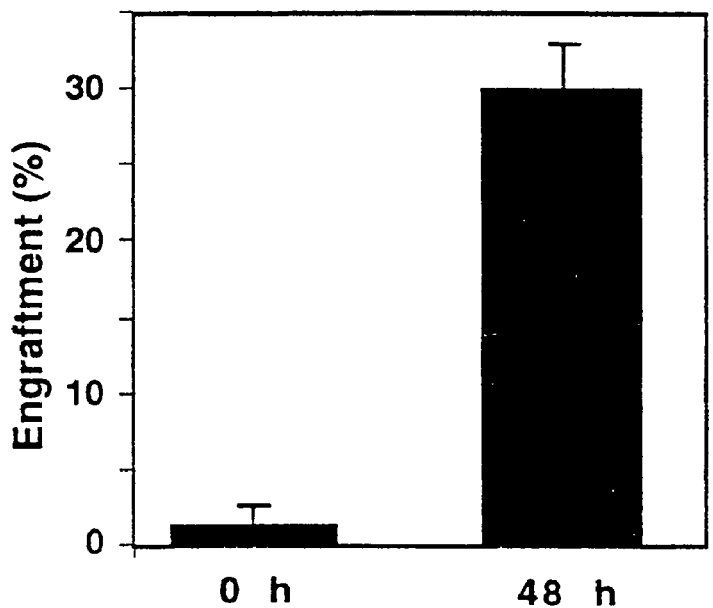
FIGS. 8A–8C show that total body irradiation results in a time-dependent increase of SDF-1 production by murine bone marrow stromal cells.
Figure 8B:
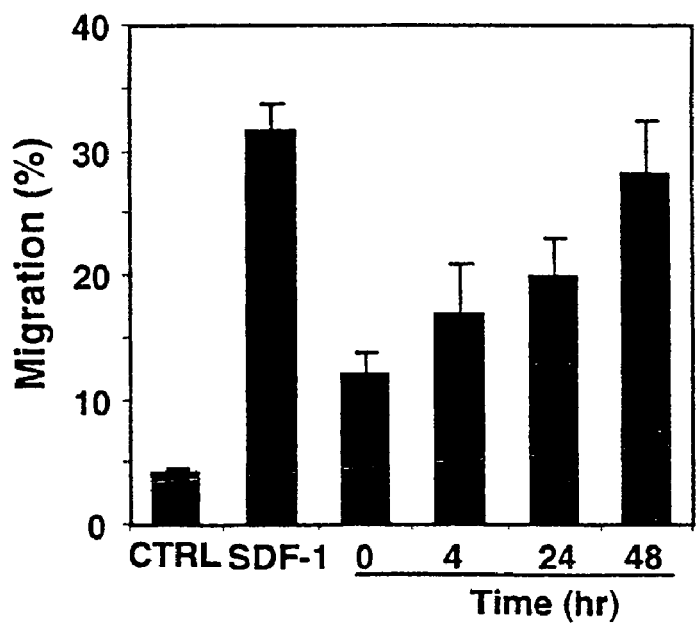

NOD/SCID mice were preconditioned by irradiation (375 rad) and human cord blood CD34$^+$CXCR4$^+$ cells (2×10$^5$) were injected to the mice immediately or 48 hours after irradiation. Mice were sacrificed after 30 days. The percentage of engraftment of human cells was assayed by staining the mouse bone marrow with antibodies to human CD45. FIG. 8A shows that the levels of engraftment increased 48 hours following irradiation. In order to study the effect of irradiation on the production of SDF-1, BM-derived fluid was collected from the bone marrow of the irradiated NOD/SCID mice immediately or 0, 4, 24, 48 hours after irradiation and tested for its ability to induce the migration of CD34$^+$ cells in a transwell migration assay with this fluid in the bottom chamber. Neutralizing antibodies to CXCR4 totally inhibited the migration towards the collected BM-derived fluid indicating that all the migratory effect found is due to SDF-1/CXCR4 interaction (data not shown). FIG. 8B shows the migration of CD34$^+$ cells toward SDF-1 (125 ng/ml), and BM-derived fluid collected at time 0, 4, 24, and 48 hours following irradiation. Background migration is shown in the control (CTRL). In order to verify the level of expression of SDF-1 in the bone marrow of irradiated NOD/SCID mice, PCR analysis of the expression of SDF-1 and of β-actin (as control) by murine bone marrow stromal cells, was carried out at different time points following irradiation (0, 2, 4, 24 and 48 hours).

The reverse transcriptase-polymerase chain reaction (RT-PCR) for SDF-I and β-actin were performed as follows: Total RNA was isolated from mice bone marrow and using TRI-Reagent (Molecular Research Center, OH) according to the manufacturer's protocol. Each RNA sample (1 µg) was subjected to cDNA synthesis in 30 µl of reaction mixture containing 1 µl Oligo dT 15 primer (500 µg/ml, Promega), 2 µl dNTP's mixture (10 mM, PCR grade, Boehringer Mannheim), 3 µl DTT (0.1 M, GibcoBRL), 1 µl RNasin (40 u/µl, Promega) and 1 µl MMLV-RT (200 u/µl, Promega) in the supplied reaction buffer (5×, 250 mM Tris-HCl, pH 8.3, 375 mM KCl, 15 mM $MgCl_2$, 50 mM DTT; Promega) for 1 h at 42° C. The PCR was performed in 50 µl reaction mixture using 5 µl of cDNA, Taq DNA Polymerase (Promega), 1 µl of dNTP's mixture (10 mM, BM) and specific primers for SDF-1 (sense 5' GGA CGC CAA GGT CGT CGC CGT G (SEQ ID NO:1), antisense 5' TTG CAT CTC CCA CGG ATG TCA G (SEQ ID NO:2); PCR product 335 bp). As a control for primer contamination or dimerization the same reaction mixture without cDNA was prepared. The levels of the house keeping gene, β-actin, were determined by the following primers (sense 5' TCC TGT GGC ATC CAT GAA ACT ACA TTC AAT TCC (SEQ ID NO:3), antisense 5' GTG AAA ACG CAG CTC AGT AAC AGT CCG CCT AG (SEQ ID NO:4); PCR product 347 bp). The amplification was performed at 64° C. for I' (35 cycles). The resulting PCR products were separated on 1.6% agarose gel (SeaKem LE agarose, FMC BioProducts).

Figure 8C:
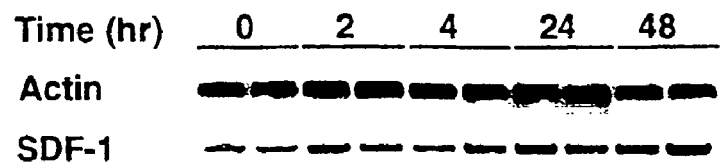

FIG. 8C shows the time-dependent over expression levels of SDF-1 in the BM of mice following irradiation. The level of actin in these samples was not changed.

This result shows for the first time a link between irradiation time dependent over expression of SDF-1 and the levels of engraftment and repopulation by hematopoietic stem cells.

Example 8

CD34$^-$ Cells Express CXCR4 and Can Migrate in Response to SDF-1

Purified cord blood CD34$^-$CD38$^-$ cells were obtained from mononuclear cells by a first depletion of CD34$^+$ by positive selection with a magnetic beads separation kit (MiniMacs) according to the manufacturer's instructions. The remaining CD34$^-$ cells (that did not bind to the magnetic beads) were further depleted from mature lineage-committed cells, including CD38$^+$ cells, with a StemSep kit (Stem Cell, Vancouver, Canada) according to the manufacturer's instructions. The remaining cells were stained for CD34 and CD38 with anti-CD34 FITC and anti-CD38 PE antibodies, respectively, and the cells were submitted to FACS analysis. FIG. 9A shows the expression of CD34 and CD38 in the CD34$^-$ cell population at the day of purification (day 0). The purified CD34$^-$CD38$^-$ cells were analyzed for their CXCR4 expression right after purification by staining with anti-CXCR4 PE antibodies (FIG. 9B). The cells were then cultured for 5 days with RPMI supplemented with 10% FCS and the cytokines SCF and IL-6 (50 ng/ml each). FIG. 9C shows an increased expression of CXCR4 after incubation of the cells for 5 days with the mixture SCF/IL-6.

Purified CD34$^-$CD38$^-$ progenitor cells untreated or treated with the mixture SCF/IL-6 for 5 days were tested for their migration capability to SDF-1 in a transwell assay. The migrating and nonmigrating cells were then tested in a colony assay for the presence of total mixed colony-forming cells. The untreated cells (Day 0) and SCF/IL-6-treated cells (Day 5) showed 11% and 45%, respectively, of total mixed colony-forming cells (FIG. 9D).

Example 9

Purging of Leukemic Stem Cells by Integrin-Dependent Migration and/or Adhesion to SDF-1

We identified herein repopulating human SRC/stem cells as functionally expressing the integrins LFA-1, VLA-4 and VLA-5 both for migratory and adhesion processes triggered by SDF-1. Furthermore, our in vitro and in vivo data suggest chemokine-dependent differential roles for these major integrins which is crucial for the multistep process of migration and engraftment.

Based on these results, it is also possible to purge malignant cells that either do not express CXCR4 and therefore will not respond to chemotactic signals mediated by SDF-1, or leukemic cells which express CXCR4 but either do not respond to SDF-1 or respond to SDF-1 in a different manner than normal cells. For example, leukemic CML cells express CXCR4, however the malignant cells have reduced migration potential to SDF-1 compared with normal cells. Within the immature CD34$^+$ compartment of newly diagnosed CML patients there is also a small minority of normal cells.

Transwell migration assays using CD34$^+$ cells from newly diagnosed CML patients to a gradient SDF-1 revealed that in the migrating population there was a three-fold increase in the levels of normal cells compared to the non-migrating cells. For example, migrating (M) and non-migrating cells from one newly diagnosed (ND) patient are presented in FIG. 10D. Moreover, after intensive chemotherapy (AT), which increases the levels of normal cells, we measured again levels of normal and leukemic cells within migrating and non-migrating CD34$^+$ cells. The percent of normal cells within the migrating population increased to 97.1% while the non migrating population had only 55% of normal cells (FIG. 10D: AT). These results demonstrate that in vitro migration to SDF-1 can be used after chemotherapy in order to purge the remaining leukemic cells by selective migration of normal cells to a gradient of SDF-1 in vitro prior to autologous transplantation. The levels of normal and leukemic cells were determined by fluorescent in situ hybridization (FISH) using bcr (green) and abl (red) specific probes which identify normal cells which have two sets of normal bcr and abl genes while leukemic cells have only one set of normal bcr and abl genes and another set of fused bcr/abl genes which is created by a translocation between chromosome 9 containing the bcr gene with chromosome 22 containing the abl gene. In each assay at least 500 cells were stained after cytospin. bcr and abl genes were visualized with specific labeled probes, which were purchased from Oncor (Gaithersburg, Md.) and used according to the manufacturer's instructions.

In addition to reduced CML cell migration to SDF-1, we have also found that immature CD34$^+$ CML cells do not express the integrin LFA-1. Normal CD34$^+$ cells and normal CD34$^+$ cells from CML patients do express LFA-1. The levels of LFA-1 expression of normal vs newly diagnosed patient CML cells, and CML cells from the same patient after intensive chemotherapy, are summarized in FIGS. 10A–10C. It is shown that normal CD34$^+$ cells express LFA-1 (FIG. 10A: NC) while newly diagnosed patient CML cells do not (FIG. 10B: ND). After intensive chemotherapy, the levels of normal cells increased to 60% and in correlation also the levels of LFA-1 increased as well (FIG. 10C: AT).

Enriched populations for LFA-1 by cell sorting using FITC-labeled anti-human LFA-1 antibodies increased the levels of normal CD34$^+$ cells to more than 99% (data not shown).

Similarly, SDF-1-mediated adhesion of LFA-1 present on CD34$^+$ cells and ICAM-1 under shear flow can be used to purge the non-adhering CML cells while maintaining the adhering normal CD34$^+$ cells (data not shown). Lastly, VLA-4 and VLA-5-dependent migration to SDF-1 across a three-dimensional extracellular-like gel to a gradient of SDF-1 was also used to purge leukemic CML cells which had significantly reduced migration potential compared with normal CXCR4$^+$ stem and progenitor cells (data not shown).

In summary, this is a new way to purge malignant cells which either do not migrate or do not activate adhesion molecules to SDF-1 or have reduced migration and adhesion potentials.

REFERENCES

1. Aiuti, A., Webb, I. J., Bleul, C., Springer, T., and Gutierrez-Ramos, J. C. (1997). The chemokine SDF-1 is a chemoattractant for human CD34$^+$ hematopoietic progenitor cells and provides a new mechanism to explain the mobilization of CD34$^+$ progenitors to peripheral blood. J. Exp. Med. 185, 111–120.
2. Bhatia, M., Bonnet D., Murdoch B. Gan, O., and Dick, J. E. (1998) A newly discovered class of human hematopoietic cells with SCID-repopulating activity. Nat. Med. 4, 1038.
3. Bleul, C. C., Farzan, M., Choe, H., Parolin, C., Clark-Lewis, I., Sosdroski, J., and Springer, T. A. (1996). The lymphocyte chemoattractant SDF-1 is a ligand for LESTR/fusin and blocks HIV entry. Nature 382, 829–832.
4. Campbell, J. J., Hedrick, J., Zlotnik, A., Siani, M. A., Thompson, D. A., and Butcher, E. C. (1998). Chemokines and the arrest of lymphocytes rolling under flow conditions. Science 279, 381–383.
5. Carr, M. W., Alon, R, and Springer, T. A. (1996). The C—C chemokine MCP-1 differentially modulates the avidity of β1 and β2 integrins on T lymphocytes. Immunity 4, 179–187.
6. Cashman, J., Bockhold, K., Hogge, D. E., Eaves, A. C., and Eaves, C. J. (1997). Sustained proliferation, multilineage differentiation and maintenance of primitive human haemopoietic cells in NOD/SCID mice transplanted with human cord blood. Br J Haematol 98, 1026–1036.
7. Civin, C. I., Porada, G. A., Lee, M. J., Terstappen, L., and Zanjani, E. D. (1996). Sustained, retransplantable, multilineage engraftment of highly purified adult human bone marrow stem cells in vivo. Blood 88, 4102–4109.
8. Conneally E., Cashman J., Petzer A., and Eaves C. J. (1997). Expansion in vitro of transplantable human cord blood stem cells demonstrated using a quantitative assay of their lympho-myeloid repopulating activity in non-obese diabetic-scid/scid mice. Proc. Natl. Acad. Sci. USA 94, 9836–9841.
9. Hirsh, E., Iglesias, A., Potocnik, A. J., Hartmann, U., and Fassler, R. (1996). Impaired migration but not differentiation of hematopoietic stem cells in the absence of β1 integrins. Nature 380, 171–175.
10. Kim, C., and Broxmeyer, H. (1998). In vitro behavior of hematopoietic progenitor cells under the influence of chemoattractants: stromal cell-derived factor-1, steel factor, and the bone marrow environment. Blood 91, 100–110.
11. Lapidot, T., Pflumio, F., Doedens, M., Murdoch, B., Williams, D. E., and Dick, J. E. (1992). Cytokine stimulation of multilineage hematopoiesis from immature human cells engrafted in SCID mice. Science 255, 1137–1141.
12. Larochelle, A., Vormoor, J., Hanenberg, H., Wang, J. C. Y., Bhatia, M., Lapidot, T., Moritz, T., Murdoch, B., Xiao, X. L., Kato, I., Williams, D. A., and Dick, J. E. (1996). Identification of primitive human hematopoietic cells capable of repopulating NOD/SCID mice using retroviral gene marking and cell purification: implications for gene therapy. Nat. Med. 2, 1329–1337.
13. Levesque, J. P., Leavesley, D. I., Niutta, S., Vadas, M., and Simmons, P. J. (1995). Cytokines increase human hemopoietic cell adhesiveness by activation of very late antigen (VLA)-4 and VLA-5 integrins. J. Exp. Med. 181, 1805–15.
14. McCune, J. M., Namikawa, R, Kaneshima, H., Shultz, L. D., Lieberman, M., and Weissman, I. L. (1988). The SCID-Hu mouse: Murine model for the analysis of human hematolymphoid differentiation and function. Science 241, 1632–1639.
15. Nagasawa, T., Hirota, S., Tachibana, K., Takakura, N., Nishikawa, S., Kitamura, Y., Yoshida, N., Kikutani, H., and Kishimoto, T. (1996). Defects of B-cell lymphopoiesis and bone-marrow myelopoiesis in mice lacking the CXC chemokine PBSF/SDF-1. Nature 382, 635–638.
16. Nolta, J. A., Hanley, M. B., and Kohn, D. B. (1994). Sustained human hematopoiesis in immunodeficient mice by cotransplantation of marrow stroma expressing human interleukin-3: Analysis of gene transduction of long-lived progenitors. Blood 83, 3041–3051.
17. Okumura, N., Tsuji, K., Ebihara, Y., Tanaka, I., Sawai, N., Koike, K., Komiyama, A., and Nakahata, T. (1996). Chemotactic and chemokinetic activities of stem cell factor on murine hematopoietic progenitor cells. Blood 87, 4100–4108.
18. Premack, B. A., and Schall, T. J. (1996). Chemokine receptors: gateways to inflammation and infection. Nature Med. 2, 1174–1178.
19. Sawada, S., Gowrishankar, K., Kitamura, R., Suzuki, M., Suzuki, G., Tahara, S., Koito, A. (1998). Disturbed CD4$^+$ T cell homeostasis and in vitro HIV-1 Susceptibility in transgenic mice expressing T cell line-tropic HIV-1 receptors. J. Exp. Med. 187, 1439–1449.
20. Signoret N., Oldridge, J., Pelchen-Matthews, A., Klasse, P. J., Tran, T., Brass, L. F., Rosenkilde, M. M., Schwartz, T. W., Holmes, W., Dallas, W., Luther, M. A., Wells, T. N., Hoxie, J. A., and Marsh, M. (1997). Phorbol esters and SDF-1 induce rapid endocytosis and down modulation of the chemokine receptor CXCR4. J. Cell Biol. 139, 651–664.
21. Spangrude, G. J., Brooks, D. M., and Tumas, D. B. (1995). Long-term repopulation of irradiated mice with limiting numbers of purified hematopoietic stem cells: in vivo expansion of stem cell phenotype but not function. Blood 85, 1006.
22. Teixido, J., and Anklesaria, P. (1992). Role of Beta 1 and beta 2 integrins in the adhesion of human CD34hi stem cells to Bone Marrow Stroma. J. Clin. Invest. 90, 358–367.
23. Zanjani, E. D., Almeida-Porada, G., Livingston, A. G., Flake, A. W., and Ogawa, M. (1998). Human bone marrow CD34$^-$ cells engraft in vivo and undergo multilineage expression that includes giving rise to CD34$^+$ cells. Exp. Hematol. 26, 353–360.

24. Zsebo, K. M., Williams, D. A., Geissler, E. N., Broudy, V. C., Martin, F. H., Atkins, H. L., Hsu, R.-Y., Birkett, N. C., Okino, K. H., Murdock, D. C., Jacobsen, F. W., Langley, K. E., Smith, K. A., Takeishi, T., Cattanach, B. M., Galli, S. J., and Suggs, S. V. (1990). Stem cell factor is encoded at the SI locus of the mouse and is the ligand for the c-kit tyrosine kinase receptor. Cell 63, 213–224.

The invention claimed is:

1. A method for the preparation of a cell composition consisting essentially of human hematopoietic $CD38^{-/low}$ $CXCR4^+$ stem cells capable of migrating in response to stromal-derived factor 1 (SDF-1), said hematopoietic $CD38^{-/low}$ $CXCR4^+$ stem cells having the capacity of migrating to, and of engraftment and repopulation of, the bone marrow in a host, comprising:

stimulating $CD38^{-/low}$ $CXCR4^{-/low}$ human stem cells for up to five days with a suitable agent capable of converting $CD38^{-/low}$ $CXCR4^{-/low}$ into $CD38^{-/low}$ $CXCR4^+$ stem cells, thus converting the $CD38^{-/low}$ $CXCR4^{-/low}$ into $CD38^{-/low}$ $CXCR4^+$ stem cells, and wherein said suitable agent is selected from the group consisting of a lectin, a cytokine, at least one type of mammalian stromal cells, and mixtures thereof, said agent being capable of converting $CD38^{-/low}$ $CXCR4^{-/low}$ into $CD38^{-/low}$ $CXCR4^+$ stem cells, and sorting out those $CD38^{-/low}$ $CXCR4^+$ human stem cells that migrate in response to SDF-1.

2. The method according to claim 1, wherein the $CD38^{-/low}$ $CXCR4^{-/low}$ stem cells are stimulated with said suitable agent for 1–2 days.

3. A method in accordance with claim 1, wherein said suitable agent is selected from the group consisting of SCF, IL-1, IL-6, IL-11, GM-CSF, and mixtures thereof.

4. The method according to claim 1, wherein said suitable agent is a member selected from the group consisting of SCF and a mixture of SCF and IL-6.

5. A method for increasing a population of hematopoietic $CXCR4^+$ stem cells for use in clinical transplantation, comprising:

up-regulating surface CXCR4 expression of hematopoietic stem cells, wherein said up-regulation is carried out by stimulation of a cellular population comprising hematopoietic CXCR4$^+$ and CXCR4$^{-/low}$ stem cells that have the potential to express CXCR4 on the cell surface, with a suitable agent, thus converting the CXCR4$^{-/low}$ into CXCR4$^+$ cells, and wherein the CXCR4$^{-/low}$ stem cells are stimulated for up to five days with a suitable agent capable of converting CXCR4$^{-/low}$ into CXCR4$^+$ stem cells, thus converting the CXCR4$^{-/low}$ into CXCR4$^+$ stem cells, and wherein said suitable agent is selected from the group consisting of a lectin, a cytokine, at least one type of mammalian stromal cells, and mixtures thereof, said agent being capable of increasing CXCR$^+$ surface expression on hematopoietic stem cells; and sorting out those CXCR4$^+$ stem cells that migrate in response to SDF-1.

6. The method according to claim 5, wherein the CXCR4$^{-/low}$ stem cells are stimulated with said suitable agent for 1–2 days.

7. A method in accordance with claim 5, wherein said suitable agent is selected from the group consisting of SCF, IL-1, IL-6, IL-11, GM-CSF, and mixtures thereof.

8. The method according to claim 5, wherein said suitable agent is a member selected from the group consisting of SCF and a mixture of SCF and IL-6.

* * * * *

SEQUENCE LISTING

```
<160> NUMBER OF SEQ ID NOS: 4

<210> SEQ ID NO 1
<211> LENGTH: 22
<212> TYPE: DNA
<213> ORGANISM: Artificial
<220> FEATURE:
<223> OTHER INFORMATION: synthetic

<400> SEQUENCE: 1
ggacgccaag gtcgtcgccg tg                                          22

<210> SEQ ID NO 2
<211> LENGTH: 22
<212> TYPE: DNA
<213> ORGANISM: Artificial
<220> FEATURE:
<223> OTHER INFORMATION: synthetic

<400> SEQUENCE: 2
ttgcatctcc cacggatgtc ag                                          22

<210> SEQ ID NO 3
<211> LENGTH: 33
<212> TYPE: DNA
<213> ORGANISM: Artificial
<220> FEATURE:
<223> OTHER INFORMATION: synthetic

<400> SEQUENCE: 3
tcctgtggca tccatgaaac tacattcaat tcc                              33

<210> SEQ ID NO 4
<211> LENGTH: 32
<212> TYPE: DNA
<213> ORGANISM: Artificial
<220> FEATURE:
<223> OTHER INFORMATION: synthetic

<400> SEQUENCE: 4
gtgaaaacgc agctcagtaa cagtccgcct ag                               32
```